(12) United States Patent
Hagiwara et al.

(10) Patent No.: US 7,949,090 B2
(45) Date of Patent: May 24, 2011

(54) X-RAY CT APPARATUS AND IMAGE RECONSTRUCTION METHOD

(75) Inventors: Akira Hagiwara, Tokyo (JP); Tsuyoshi Ogata, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 480 days.

(21) Appl. No.: 12/241,579

(22) Filed: Sep. 30, 2008

(65) Prior Publication Data

US 2009/0086888 A1    Apr. 2, 2009

(30) Foreign Application Priority Data

Oct. 2, 2007  (JP) ................................. 2007-258483

(51) Int. Cl.
A61B 6/03    (2006.01)

(52) U.S. Cl. .............................................. 378/15; 378/4

(58) Field of Classification Search ................ 378/4, 15, 378/19–20, 901

See application file for complete search history.

(56) References Cited

U.S. PATENT DOCUMENTS

| | | | |
|---|---|---|---|
| 4,580,219 A | 4/1986 | Pelc et al. | |
| 5,612,985 A | 3/1997 | Toki et al. | |
| 5,640,436 A | 6/1997 | Kawai et al. | |
| 6,061,421 A | 5/2000 | Hagiwara | |
| 6,430,253 B1 | 8/2002 | Oikawa | |
| 6,434,214 B1 | 8/2002 | Kawai et al. | |
| 6,463,118 B2 | 10/2002 | Besson | |
| 6,658,082 B2 | 12/2003 | Okumura et al. | |
| 6,795,522 B2 | 9/2004 | Nishide et al. | |
| 6,925,141 B2 | 8/2005 | Bruder et al. | |
| 6,931,094 B2 | 8/2005 | Li | |
| 7,173,997 B2 | 2/2007 | Hagiwara | |
| 7,397,889 B2 | 7/2008 | Kobayashi et al. | |
| 2005/0008116 A1 | 1/2005 | Nishide et al. | |
| 2005/0094761 A1* | 5/2005 | Hagiwara | ....................... 378/15 |

FOREIGN PATENT DOCUMENTS

JP         2005-040582        2/2005

* cited by examiner

*Primary Examiner* — Edward J Glick
*Assistant Examiner* — John M Corbett
(74) *Attorney, Agent, or Firm* — Armstrong Teasdale LLP

(57) ABSTRACT

An X-ray CT apparatus is provided for reducing the amount of computation at image reconstruction thereby to shorten an image reconstruction time. The X-ray CT apparatus comprises a cradle which moves in a horizontal direction to convey a subject to a photography space, an X-ray detector comprising a plurality of detecting element rows, for obtaining projection data by a helical scan when the cradle is moved under acceleration/deceleration and at a constant velocity, and backprojection processing device for performing a backprojection process on the projection data. When image reconstruction is carried out using the projection data acquired when the cradle is moved under acceleration/deceleration, the backprojection processing device assumes a virtual image reconstruction plane P' where the cradle is assumed to be moved at the constant velocity, with respect to an image reconstruction plane P of each view and backprojects projection data onto the virtual image reconstruction plane P'.

20 Claims, 23 Drawing Sheets

X-RAY CT APPARATUS AND IMAGE RECONSTRUCTION METHOD

CROSS REFERENCE TO RELATED APPLICATIONS

This application claims the benefit of Japanese Patent Application No. 2007-258483 filed Oct. 2, 2007, which is hereby incorporated by reference in its entirety.

BACKGROUND OF THE INVENTION

The subject matter disclosed herein relates to an X-ray CT (Computerized Tomography) apparatus, and particularly to an X-ray CT apparatus capable of reducing the amount of computation when image reconstruction is carried out using projection data acquired when a cradle is moved under acceleration/deceleration upon a helical scan.

When the acquisition of projection data used in image reconstruction is performed by a helical scan in an X-ray CT apparatus, an X-ray tube and an X-ray detector comprised of a plurality of X-ray detecting elements are rotated about a subject, and a cradle with the subject placed thereon is moved linearly.

There is also a case where the acquisition of projection data is carried out only during a period in which the travel velocity of the cradle is maintained constant, of a linear travel distance of the cradle. There is, however, also a case where as described in, for example, Japanese Unexamined Patent Publication No. 2005-40582, projection data are acquired even when the cradle is being accelerated/decelerated. Carrying out the acquisition of projection data using even the travel distance for acceleration/deceleration, of the linear travel distance of the cradle in this way makes it possible to acquire the projection data at a short travel distance and perform the acquisition of the projection data in a short period of time.

BRIEF DESCRIPTION OF THE INVENTION

When, however, the acquisition of the projection data is carried out using even the travel distance for acceleration/deceleration, of the linear travel distance of the cradle, the amount of computation at the image reconstruction increases because the cradle is not at a constant velocity.

One example of an increase in the amount of computation where the image reconstruction is carried out using the projection data acquired when the cradle is moved under acceleration/deceleration will be explained. Upon the image reconstruction, a backprojection process is performed in which projection data are added corresponding to pixels to generate backprojection data. There is a case where as this backprojection process, pixel points on an image reconstruction plane and projection data corresponding to the pixel points are specified or identified to perform a backprojection process.

When the image reconstruction is done here using the projection data acquired when the cradle is moved at the constant velocity, the distance between an image reconstruction plane at a given view and the center in a z-axis direction, of the X-ray detector is always kept constant without differing for each image reconstruction plane. Thus, X-ray detecting elements each of which detects X-rays penetrated through a specific pixel on the image reconstruction plane, always become the same one where attention is given to a specific view. Therefore, when the pixel points on the image reconstruction plane and the projection data corresponding to the pixel points are specified or identified upon the backprojection process where the image reconstruction is performed using the projection data acquired when the cradle is moved at the constant velocity, tables in which pixel points on image reconstruction planes and X-ray detecting elements corresponding to the pixel points are defined are stored every view, and they are specified with reference to the tables.

On the other hand, when the image reconstruction is carried out using projection data acquired upon movement of the cradle under acceleration/deceleration at which the velocity of the cradle is not constant, the distance between an image reconstruction plane at a given view and the center in a z-axis direction, of the X-ray detector differs for each image reconstruction plane and is not always kept constant. Thus, X-ray detecting elements each of which detects X-rays penetrated through a specific pixel on the image reconstruction plane are not always brought to the same one at a specific view. Therefore, when pixel points on each image reconstruction plane and projection data corresponding to the pixel points are specified or identified upon a backprojection process where image reconstruction is done using the projection data acquired when the cradle is moved under acceleration/deceleration, the tables cannot be used and their identification by computation is forced every pixel point. Thus, the amount of computation increases and the time taken for image reconstruction has become long.

A problem to be solved by the present invention is to provide an X-ray CT apparatus capable of reducing the amount of computation at image reconstruction thereby to shorten the time taken for the image reconstruction.

The present invention has been made to solve the above problem. The invention according to a first aspect provides an X-ray CT apparatus comprising a cradle which moves in a horizontal direction to convey a subject to a photography space, an X-ray detector comprising a plurality of detecting element rows, for obtaining projection data by a helical scan when the cradle is moved under acceleration/deceleration and at a constant velocity, and backprojection processing device for performing a backprojection process on the projection data, wherein when image reconstruction is carried out using the projection data acquired when the cradle is moved under acceleration/deceleration, the backprojection processing device assumes a virtual image reconstruction plane where the cradle is assumed to be moved at the constant velocity, with respect to an image reconstruction plane of each view and backprojects projection data onto the virtual image reconstruction plane.

The invention according to a second aspect provides an X-ray CT apparatus wherein in the X-ray CT apparatus according to the first aspect, it further includes relocation processing device which performs a relocation with raw data corresponding to a specific pixel on the image reconstruction plane as raw data about each pixel on the virtual image reconstruction plane, corresponding to the specific pixel and which performs the relocation process on each raw data at projection data of the specific view to generate relocated projection data and generates the relocated projection data with respect to all views, and storage unit which stores therein tables in which pixel points on the virtual image reconstruction plane and X-ray detecting elements corresponding to the pixel points, wherein the backprojection processing device specifies pixel points on the virtual image reconstruction plane and projection data corresponding to the pixel points with respect to the relocated projection data by referring to the tables thereby to perform a backprojection process.

The invention according to a third aspect provides an X-ray CT apparatus wherein in the X-ray CT apparatus according to the second aspect, it further includes interpolation processing device for performing an interpolation process on the relocated projection data, and the backprojection processing device specifics pixel points on the virtual image reconstruction plane and projection data corresponding to the pixel points with respect to the relocated projection data subsequent to the interpolation process by referring to the tables thereby to perform a backprojection process.

The invention according to a fourth aspect provides an X-ray CT apparatus wherein in the X-ray CT apparatus according to the second or third aspect, it further includes weighting processing device which multiplies the projection data by reconstruction weights to generate weighted projection data every view, and the relocation processing device performs a relocation process on each raw data at the weighted projection data.

The invention according to a fifth aspect provides an X-ray CT apparatus wherein in the X-ray CT apparatus according to the fourth aspect, the weighting processing device specifies or identifies to which pixel on the image reconstruction plane each raw data at the projection data corresponds and thereafter performs a multiplication process of a cone beam reconstruction weight to generate weighted projection data.

The invention according to a sixth aspect provides an X-ray CT apparatus wherein in the X-ray CT apparatus according to the fourth aspect, the weighting processing device multiplies respective projection data about opposite views with an image reconstruction plane interposed therebetween or two views different at 360° from each other by weight coefficients each based on a distance between the X-ray detector having detected the projection data and the image reconstruction plane as the reconstruction weights to generate weighted projection data every view.

The invention according to a seventh aspect provides an X-ray CT apparatus wherein in the X-ray CT apparatus according to the second aspect, it further includes weighting processing device which multiplies the relocated projection data by reconstruction weights after the relocation process to generate weighted relocated projection data, and the backprojection processing device performs a backprojection process on the weighted relocated projection data.

The invention according to an eighth aspect provides an X-ray CT apparatus wherein in the X-ray CT apparatus according to the second aspect, it further includes weighting processing device which multiplies the relocated projection data by reconstruction weights after the relocation process to generate weighted relocated projection data, and interpolation processing device which performs an interpolation process on the weighted relocated projection data, and the backprojection processing device performs a backprojection process on the relocated projection data subjected to the weighting process and the interpolation process.

The invention according to a ninth aspect provides an X-ray CT apparatus wherein in the X-ray CT apparatus according to the second aspect, it includes interpolation processing device which performs an interpolation process on the relocated projection data after the relocation process, and weighting processing device which multiplies the relocated projection data subjected to the interpolation process by reconstruction weights to perform a weighting process, and the backprojection processing device performs a backprojection process on the relocated projection data subjected to the interpolation process and the weighting process.

The invention according to tenth aspect provides an X-ray CT apparatus wherein in the X-ray CT apparatus according to the seventh, eighth or ninth aspect, the weighting processing device specifies to which pixel on the image reconstruction plane prior to the relocation process each raw data at the relocated projection data corresponds and thereafter performs a multiplication process of a cone beam reconstruction weight to generate weighted relocated projection data.

The invention according to an eleventh aspect provides an X-ray CT apparatus wherein in the X-ray CT apparatus according to the seventh, eighth or ninth aspect, the weighting processing device multiplies respective relocated projection data about opposite views with the virtual image reconstruction plane interposed therebetween or two views different at 360° from each other by weight coefficients each based on a distance between the X-ray detector having detected the projection data prior to the relocation, corresponding to the relocated projection data and the image reconstruction plane as the reconstruction weights to generate weighted relocated projection data.

According to the X-ray CT apparatus related to the invention of the first aspect, when image reconstruction is done using projection data acquired when the cradle is moved under acceleration/deceleration, a backprojection process is performed assuming a virtual image reconstruction plane where the cradle is assumed to move at a constant velocity. Therefore, the amount of computation at the image reconstruction using the projection data acquired when the cradle is moved under acceleration/deceleration, can be reduced than conventional.

According to the X-ray CT apparatus related to the invention of the second aspect, a relocation process is effected on each raw data at projection data acquired when the cradle is moved under acceleration/deceleration, whereby each pixel point on the virtual image reconstruction plane and projection data corresponding to the pixel point are specified or identified with reference to the tables in the backprojection process step, thereby to make it possible to perform a backprojection process. Consequently, a computation for identifying or specifying the pixel point lying on the image reconstruction plane and the projection data corresponding to the pixel point becomes unnecessary at the backprojection process step. On the other hand, when a relocation process is performed with raw data corresponding to a specific pixel on the image reconstruction plane as raw data about each pixel on the virtual image reconstruction plane, corresponding to the specific pixel, it is necessary to perform the computation of position determination or identification about whether the raw data should be relocated as raw data of a detecting element row at any position, that is, the computation of position identification of the detecting element row corresponding to each pixel on the virtual image reconstruction plane. However, this computation corresponds to a computation in units of raw data, i.e., units of pixel rows. The amount of computation is low as compared with the case where computation is done every pixel point at the backprojection process as in the conventional case. Thus, the amount of computation over the entire image reconstructing process can be reduced than conventional, whereby the time taken for image reconstruction can be shortened.

According to the X-ray CT apparatus related to the invention of the third aspect, an interpolation process is performed on the relocated projection data, thereby to make it possible to suppress degradation in image quality.

According to the X-ray CT apparatus related to the invention of the fourth aspect, a relocation process is performed on each raw data at the weighted projection data, thereby to make it possible to obtain weighted relocated projection data. Thereafter, a backprojection process is carried out, thereby to make it possible to obtain an effect similar to the invention of the first aspect.

According to the X-ray CT apparatus related to the invention of the fifth aspect, each of the projection data is multiplied by its corresponding cone beam reconstruction weight as the reconstruction weight to generate weighted projection data. A relocation process is performed on each raw data at the projection data. Thereafter, a backprojection process is performed, thereby to make it possible to obtain an effect similar to the invention of the first aspect.

According to the X-ray CT apparatus related to the invention of the sixth aspect, respective projection data about opposite views with an image reconstruction plane interposed therebetween or two views different at 360° from each other are respectively multiplied by weight coefficients each based on a distance between the X-ray detector having detected the projection data and the image reconstruction plane as the reconstruction weights to generate weighted projection data. The relocation process is performed on each raw data at the projection data. Thereafter, a backprojection process is carried out, thereby to make it possible to obtain an effect similar to the invention of the first aspect.

According to the X-ray CT apparatus related to the invention of the seventh aspect, a weighting process is performed after the relocation process step, thereby to make it possible to obtain weighted relocated projection data. Thereafter, the backprojection process step is executed, thereby to make it possible to obtain an effect similar to the invention of the first aspect.

According to the X-ray CT apparatus related to the inventions of the eighth and ninth aspects, relocated projection data subjected to a weighting process and an interpolation process can be obtained. Thereafter, a backprojection process is executed, thereby to make it possible to obtain an effect similar to the invention of the firs aspect.

According to the X-ray CT apparatus related to the invention of the tenth aspect, a multiplication process of a cone beam reconstruction weight is performed to generate weighted relocated projection data. Thereafter, a backprojection process is carried out, thereby to make it possible to obtain an effect similar to the invention of the first aspect.

According to the X-ray CT apparatus related to the invention of the eleventh aspect, respective relocated projection data about opposite views with the virtual image reconstruction plane interposed therebetween or two views different at 360° from each other are respectively multiplied by weight coefficients each based on a distance between the X-ray detector having detected the projection data prior to the relocation, corresponding to the relocated projection data and the image reconstruction plane as the reconstruction weights to generate weighted relocated projection data. Thereafter, a backprojection process is carried out, thereby to make it possible to obtain an effect similar to the invention of the first aspect.

BRIEF DESCRIPTION OF THE DRAWINGS

FIGS. 13(A) and 13(B) show the X-ray tube, X-ray detector and image reconstruction plane as viewed from the x-axis direction, wherein FIG. 13(A) is a diagram showing a real image reconstruction plane at a noted view at acceleration/deceleration movement of the cradle, and FIG. 13(B) is a diagram showing a virtual image reconstruction plane at a noted view where the cradle is moved at a constant velocity.

FIGS. 19(A) and 19(B) are diagrams illustrating an X-ray tube and an X-ray detector and a real image reconstruction plane at a noted view at acceleration/deceleration movement of a cradle, wherein FIG. 19(A) is a diagram as viewed from an x-axis direction, and FIG. 19(B) is a diagram as viewed from a z-axis direction.

FIGS. 20(A) and 20(B) are diagrams illustrating the X-ray tube and X-ray detector and a real image reconstruction plane at a noted view where the cradle is assumed to have moved at a constant velocity, wherein FIG. 20(A) is a diagram as viewed from an x-axis direction, and FIG. 20(B) is a diagram as viewed from a z-axis direction.

DETAILED DESCRIPTION OF THE INVENTION

Embodiments of the present invention will hereinafter be described in detail based on the accompanying drawings.

Figure 1:
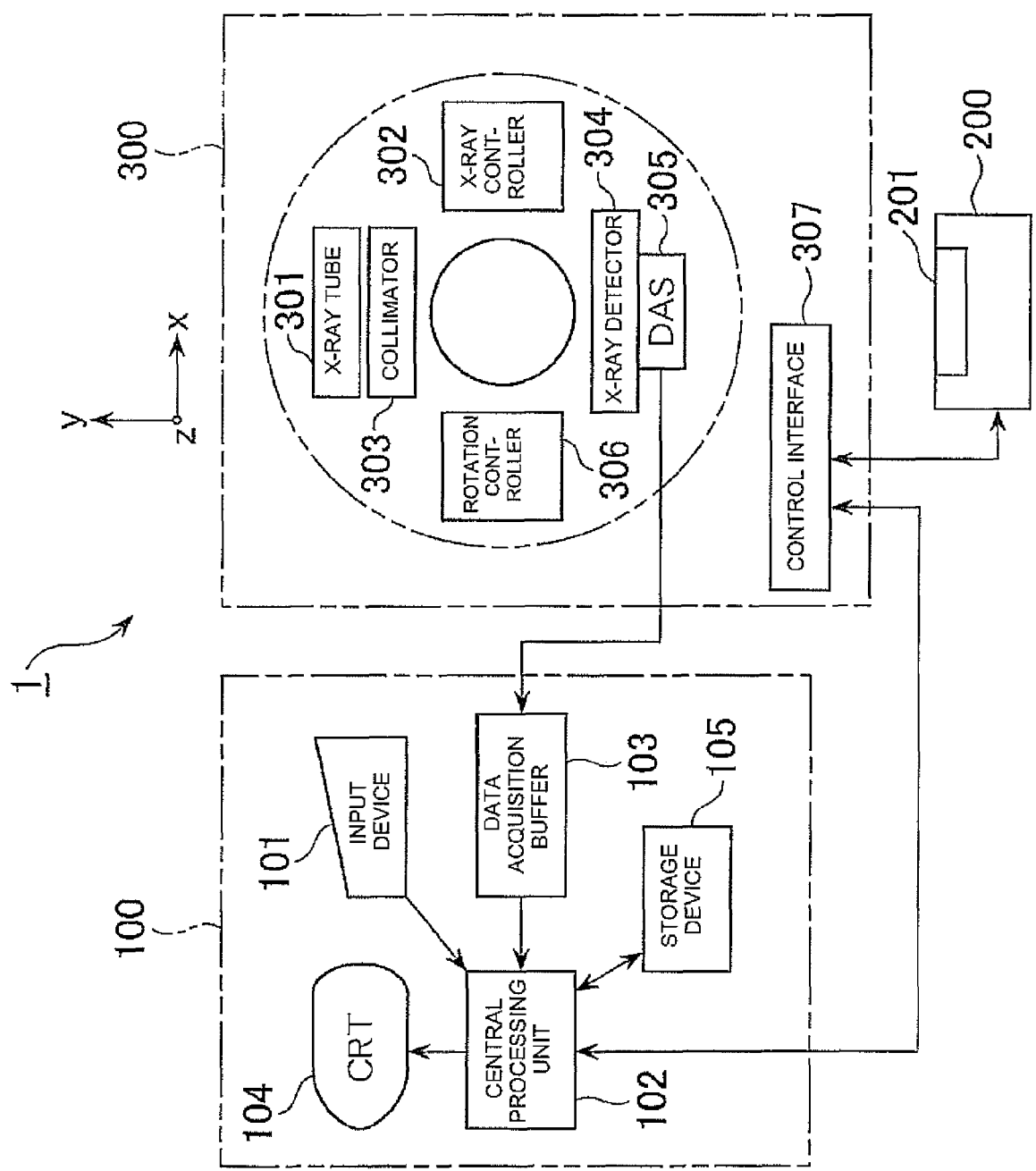
FIG. 1 is a block diagram showing a construction of an X-ray CT apparatus according to a first embodiment of the present invention.

A first embodiment of the present invention will first be explained. FIG. 1 is a block diagram showing a construction of an X-ray CT apparatus according to the first embodiment of the present invention.

The X-ray CT apparatus 1 shown in FIG. 1 is equipped with an operation console 100, a table device 200 and a scan gantry 300.

Figure 2:
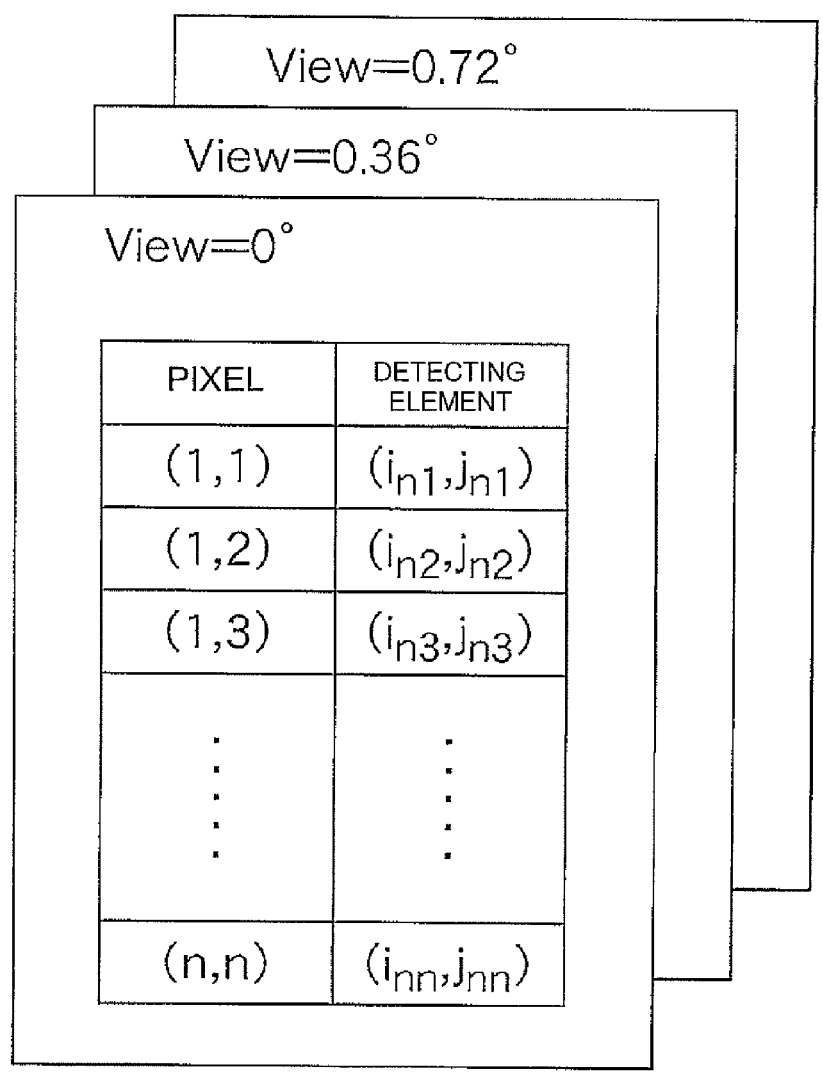
FIG. 2 is a diagram showing tables for specifying pixel points on an image reconstruction plane and projection data corresponding to the pixel points.

The operation console 100 has an input device 101 which receives an input from an operator, a central processing unit 102 which executes an image reconstructing process and the like, a data acquisition buffer 103 which acquires or collects detection data every X-ray detecting element (to be described later) acquired by the scan gantry 300 and sets the same as projection data, a CRT 104 which displays a CT image reconstructed from the projection data, and a memory or storage device 105 which stores programs, data, X-ray CT images, etc. therein. In the present embodiment, tables shown in FIG. 2 are stored every view as the data stored in the storage device 105. Pixel points lying on an image reconstruction plane and the X-ray detecting elements (detecting elements for detecting X rays penetrated through the pixel points) corresponding to the pixel points where scanning is done when a cradle 201 (to be described later) at the table device 200 is moved at a constant velocity to acquire projection data, are defined in the tables.

The tables are referred to when pixel points lying on an image reconstruction plane and projection data corresponding to the pixel points are specified upon a backprojection process at the time that image reconstruction is performed using the projection data acquired when the cradle 201 is moved at the constant velocity. As will be described in detail later, the tables are referred to even upon a backprojection process at the time that image reconstruction is carried out using projection data acquired when the cradle 201 is moved under acceleration/deceleration. In this case, the tables have significance assuming that pixel points on a virtual image reconstruction plane P' to be described later and X-ray detecting elements corresponding to the pixel points have been defined.

Figure 3:
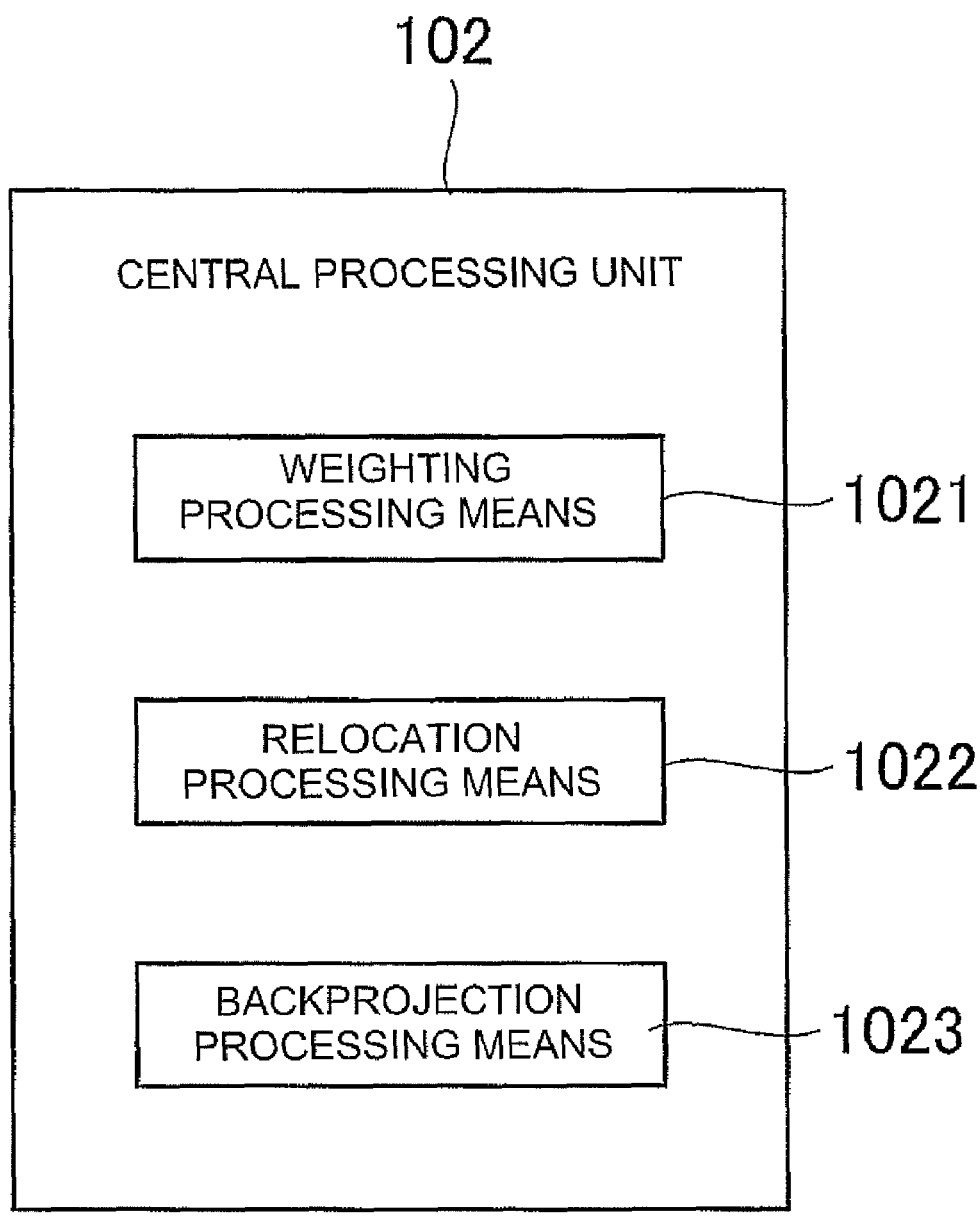
FIG. 3 is a block diagram illustrating a construction of a central processing unit.

The central processing unit 102 comprises, for example, a computer or the like and includes weighting processing device 1021 for performing a weighting process to be described later, relocation processing device 1022 for performing a relocation process to be described later, and backprojection processing device 1023 for performing a backprojection process to be described later, as shown in FIG. 3. Although not shown in the figure, the central processing unit 102 is equipped with pre-processing device for performing pre-processing to be described later, and filter processing device for performing a filter process to be described later.

The table device 200 has the cradle 201 which inserts and draws a subject into and from a cavity portion or aperture of the scan gantry 300 with the subject placed thereon. The cradle 201 is moved in the horizontal direction to insert and draw the subject into and from the cavity portion of the scan gantry 300.

The scan gantry 300 includes an X-ray tube 301, an X-ray controller 302, a collimator 303, an X-ray detector 304, a DAS (Data Acquisition System) 305, a rotation controller 306 which rotates the X-ray tube 301 and the X-ray detector 304 about a body axis of the subject, and a control interface 307 which swaps control signals or the like with the operation console 100 and the table device 200.

Figure 4:
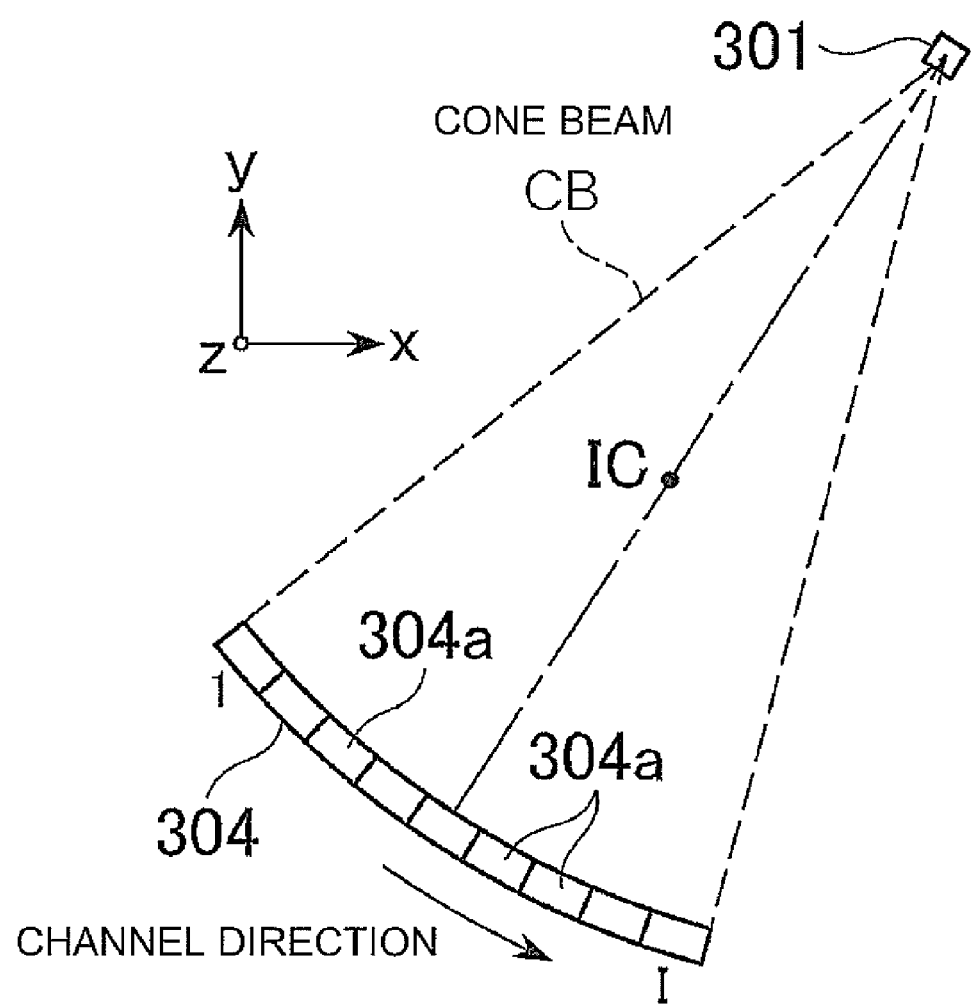
FIG. 4 is a diagram for describing an X-ray tube and an X-ray detector.
Figure 5:
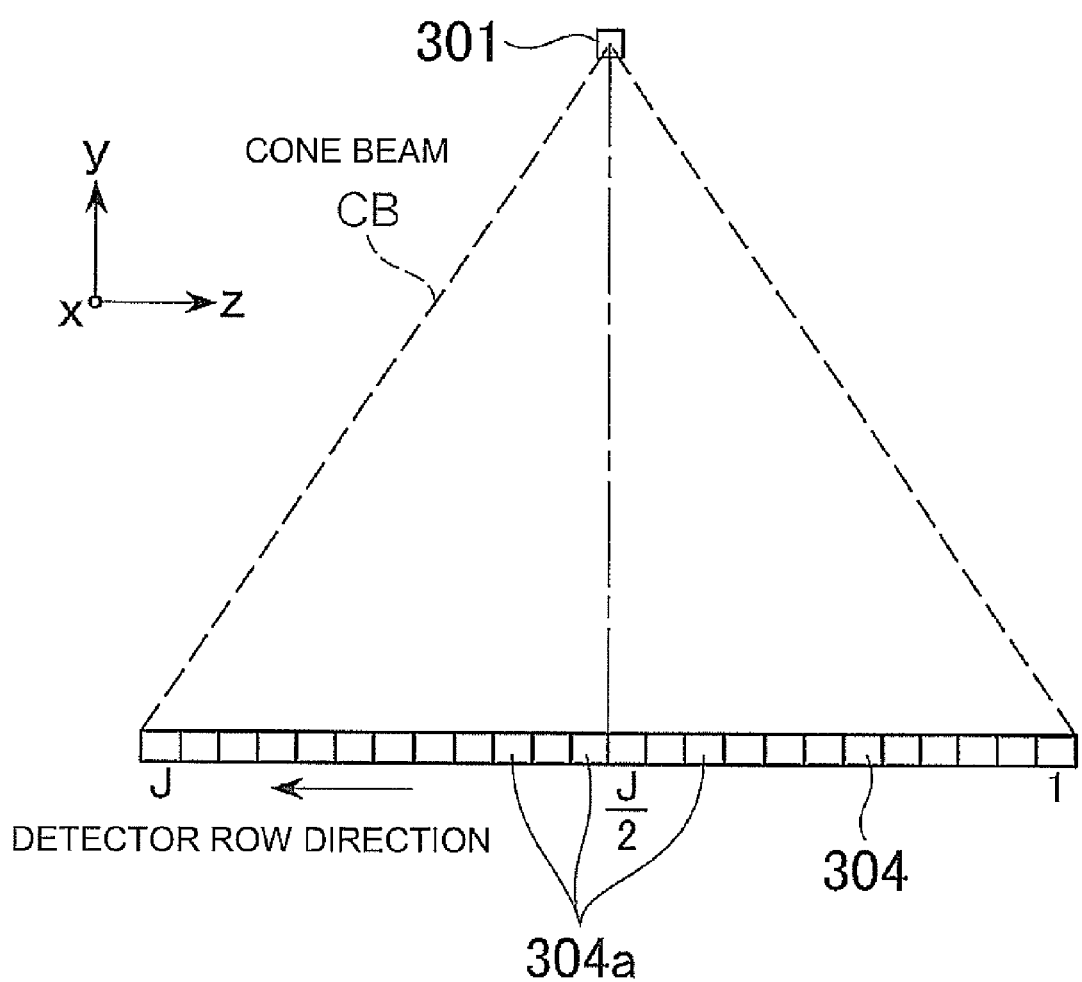
FIG. 5 is a diagram for describing the X-ray tube and the X-ray detector.

FIGS. 4 and 5 are respectively diagrams for describing the X-ray tube 301 and the X-ray detector 304. The X-ray tube 301 and the X-ray detector 304 rotate about the center of rotation IC. When the vertical direction is assumed to be a y direction, the horizontal direction is assumed to be an x direction and the direction orthogonal to these is assumed to be a z direction, the plane at which the X-ray tube 301 and the X-ray detector 304 are rotated, is an xy plane. The direction in which the cradle 12 is moved, corresponds to the z direction.

The X-ray tube 301 generates an X-ray beam called a cone beam CB. When the direction of a central axis of the cone beam CB is parallel to the y direction, this is defined as view=0°.

The X-ray detector 304 comprises a plurality of X-ray detecting elements 304a. Described in more detail, the X-ray detector 304 has a plurality of detecting element rows, i.e., a first detecting element row through a Jth (where $J \geqq 2$) detecting element row. Each of the detecting element rows has a plurality of channels, i.e., a channel 1 through a channel I (where $I \geqq 2$). For example, the X-ray detector 304 has detecting element rows (i.e., J=256) corresponding to 256 rows, and channels (i.e., I=1024) corresponding to 1024 channels.

An imaging method of the X-ray CT apparatus 1 constructed in this way will be explained. In the X-ray CT apparatus 1, projection data are acquired when the cradle 201 is moved under acceleration/deceleration and moved at the constant velocity upon a helical scan, and image reconstruction is carried out using the obtained projection data. A description will be made of the case where the image reconstruction is performed using the projection data acquired when the cradle 201 is moved under acceleration/deceleration. The image reconstruction using the projection data acquired when the cradle 201 is moved at the constant velocity, is similar to the image reconstruction using the projection data acquired when the cradle 201 is moved under acceleration/deceleration, except that a relocation process of Step S5 to be described later is not conducted. The description thereof will be omitted herein.

Figure 6:
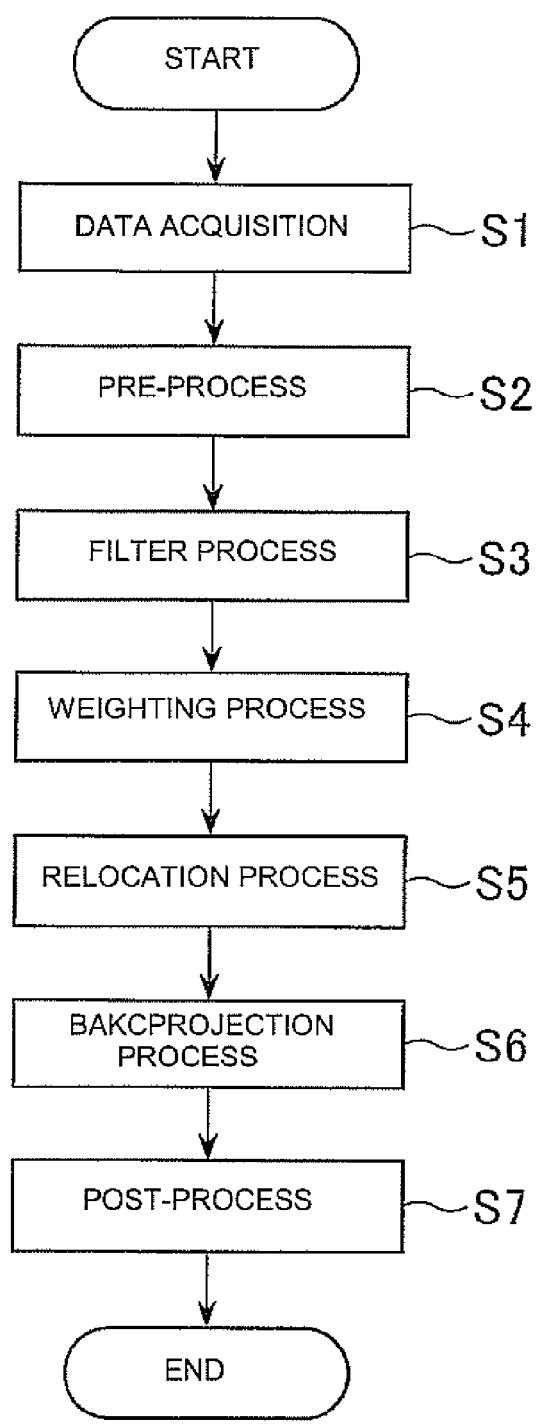
FIG. 6 is a flowchart showing an imaging method of the X-ray CT apparatus according to the first embodiment.
Figure 7:
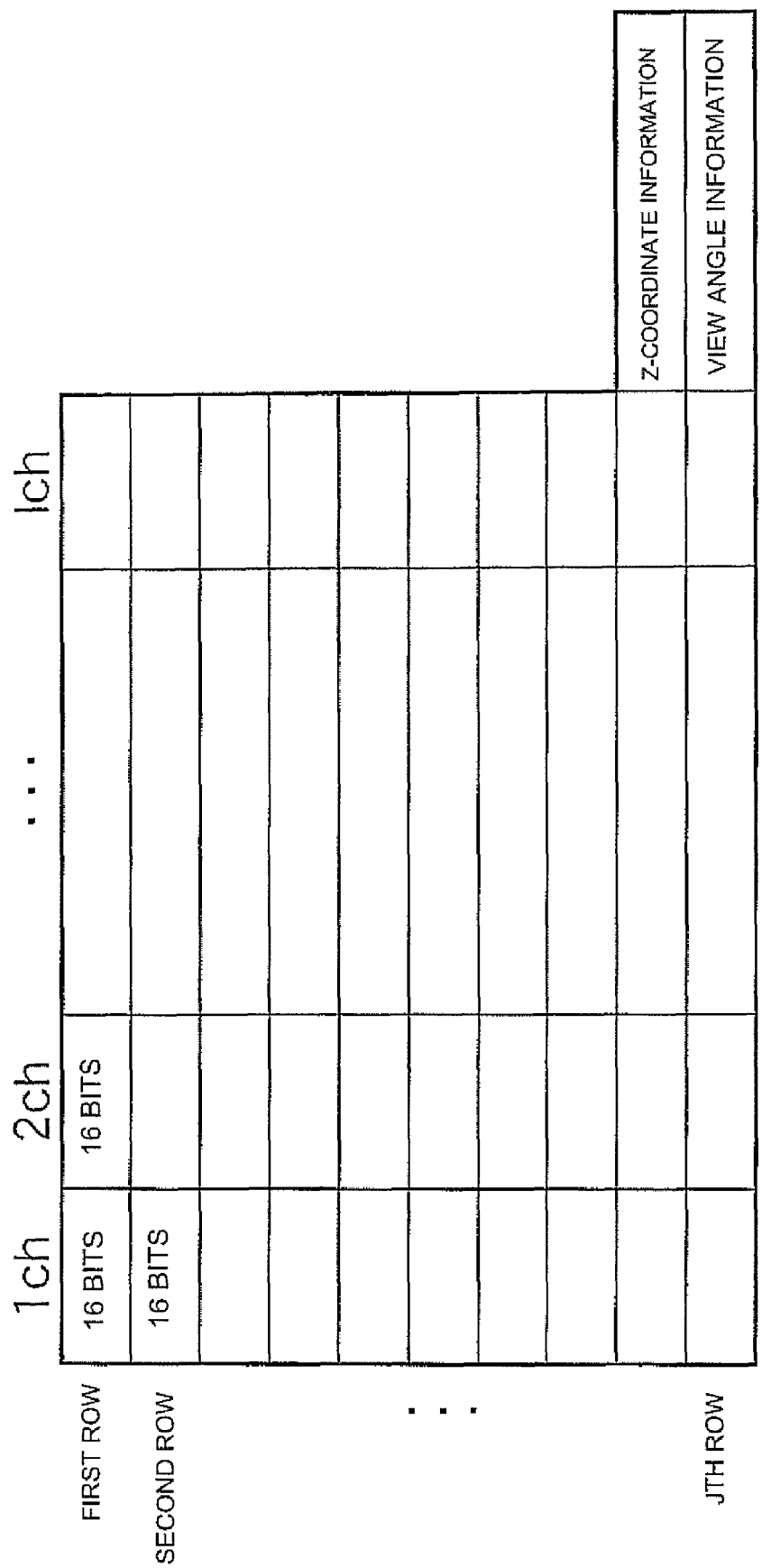
FIG. 7 is a diagram illustrating a format of projection data of a given view angle view.

FIG. 6 is a flowchart showing the imaging method of the X-ray CT apparatus 1 according to the first embodiment. At Step S1 shown in FIG. 6, projection data every view angle view represented by a linear travel position z, a view angle, a detector row number j and a channel number i are acquired or collected while the X-ray tube 301 and the X-ray detector 304 are being rotated about the subject and the cradle 201 is being moved linearly. A format of projection data at a given view angle view is shown in FIG. 7. The projection data is an aggregation or collection of detection data obtained every X-ray detecting element 304a referred to above and is stored in the storage device 105 every view angle view (every 0.36° in the case of 1000 views in all, for example).

Figure 8:
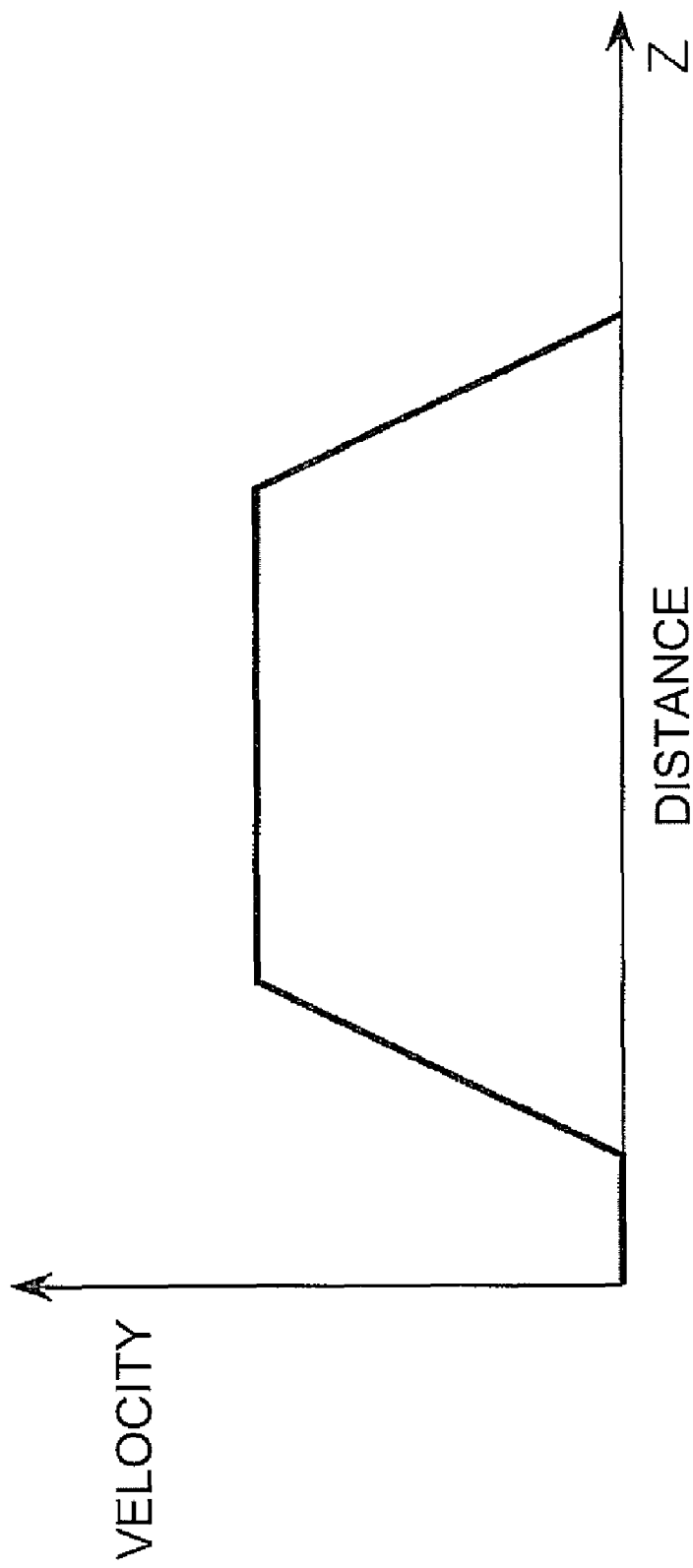
FIG. 8 is a diagram showing the relationship between a linear travel distance of a cradle and a linear travel velocity thereof.

The central processing unit 102 performs control on the movement of the cradle 201. FIG. 8 is a diagram showing the relationship between a linear travel distance of the cradle 201 and a linear travel velocity thereof. The control on the movement of the cradle 201 will be described in detail based on the FIG. 8. The central processing unit 102 accelerates the cradle 201 based on a predetermined function. When the cradle 201 reaches a predetermined linear travel velocity, the central processing unit 102 moves it at a constant velocity. Next, when the cradle 201 reaches a constant-velocity end position, the central processing unit 102 decelerates it based on a predetermined function. When the linear travel velocity of the cradle 201 reaches a stoppable velocity, the central processing unit 102 stops the linear movement of the cradle 201.

Referring back to FIG. 6, the central processing unit 102 performs image reconstruction at Step S2 and later. The image reconstruction used herein is of three-dimensional image reconstruction. Described specifically, at Step S2, the pre-processing device (not shown) first performs pre-processing (offset correction, logarithmic correction, X-ray dose correction and sensitivity correction) on the projection data.

At Step S3, the filter processing device (not shown) performs a filter process on the projection data subjected to the pre-processing. That is, the projection data is subjected to Fourier transform and multiplied by a filter (reconstruction function), followed by being subjected to inverse Fourier transform.

At Step S4, the weighting processing device 1021 performs a weighting process on the projection data subjected to the filter process. The weighting process will be described later with reference to FIG. 9.

At Step S5, the relocation processing device 1022 performs a relocation process on the projection data subjected to the weighting process to obtain relocated projection data. The relocation process will be described later with reference to FIG. 12.

At Step S6, the backprojection processing device 1023 performs a backprojection process on the relocated projection data to obtain backprojection data. The backprojection process will be described later with reference to FIG. 16.

At Step S7, a post-process is performed on the backprojection data to obtain a CT image.

Figure 9:
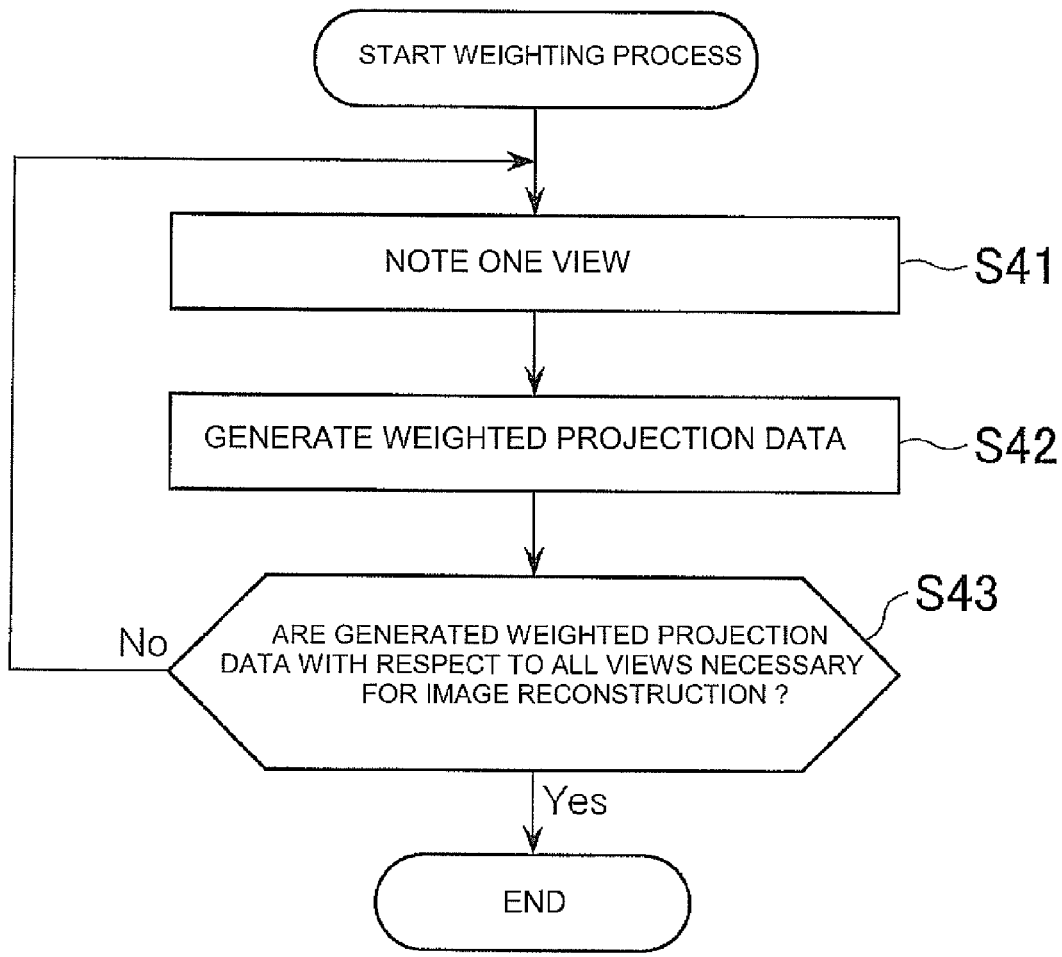
FIG. 9 is a flowchart illustrating the details of a weighting process.

The weighting process of Step S4 will be explained in detail. FIG. 9 is a flowchart showing the details of the weighting process.

At Step S41, attention is given to one of all views (i.e., views corresponding to 360° or views corresponding to "180°+fan angles") necessary for reconstruction of a CT image.

At Step S42, to which pixel on the image reconstruction plane projection data for each detecting element row unit, i.e., raw data corresponds, is computed. After the computation thereof, the raw data is multiplied by a cone beam reconstruction weight to generate or produce weighted raw data. The weighted raw data is generated for each raw data to obtain weighted projection data (multiplication process of cone beam reconstruction weight).

Figure 10:
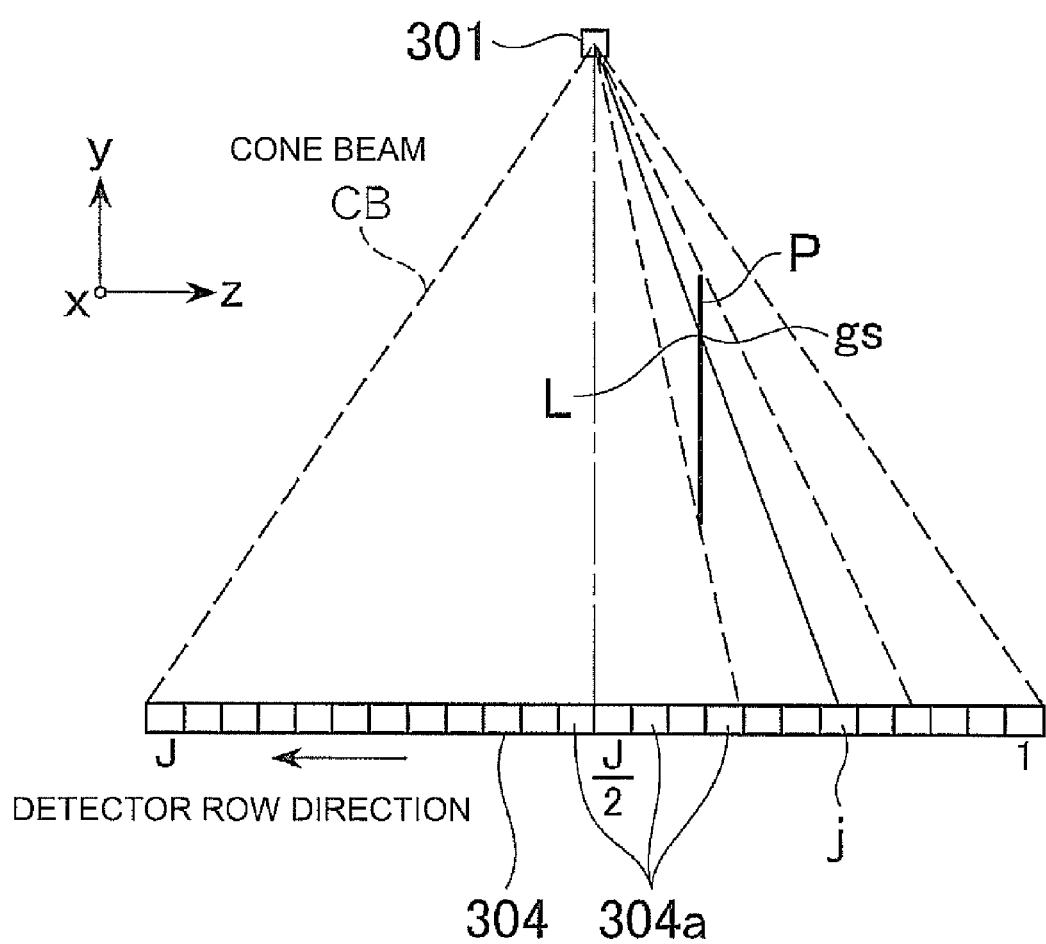
FIG. 10 is a diagram showing the X-ray tube, the X-ray detector and the image reconstruction plane as viewed from an x-axis direction.
Figure 11:
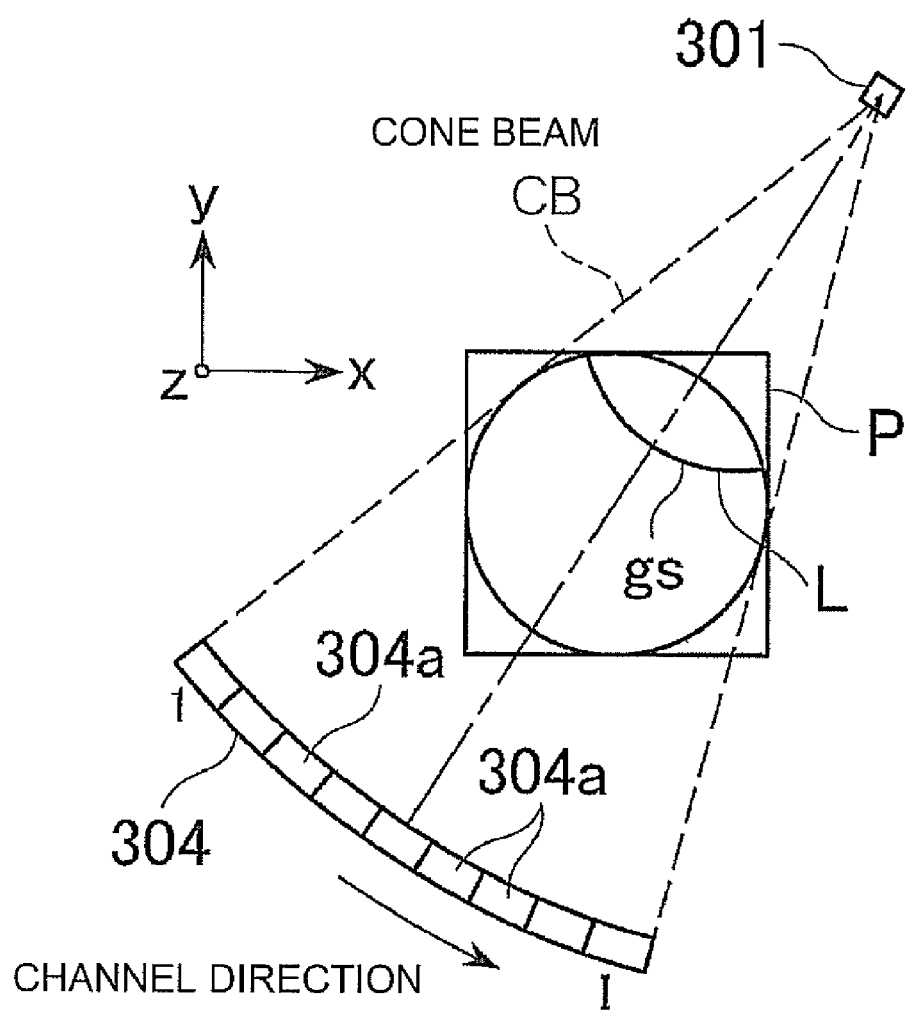
FIG. 11 is a diagram related to FIG. 10 as viewed from a z-axis direction thereof.

Step S42 referred to above will be explained in some more detail with reference to FIGS. 10 and 11. FIG. 10 is a diagram showing the X-ray tube 301 and the X-ray detector 304 and an image reconstruction plane P as viewed from an x-axis direction, and FIG. 11 is a diagram related to FIG. 10 as viewed from a z-axis direction thereof. A distribution L of raw data of a specific detecting element row j projected onto the image reconstruction plane P is shown in these figures. At Step S42 referred to above, a pixel group gs equivalent to the distribution L is specified by calculation. Thereafter, the raw data is multiplied by a cone beam reconstruction weight to generate weighted raw data. Then, the weighted raw data is generated for all raw data projected onto the image reconstruction plane P to obtain weighted projection data.

Here, the cone beam reconstruction weight is calculated based on, for example, the distance from the focal point of the X-ray tube 301 to the detecting element row j corresponding to the raw data L.

At Step S43, Steps S41 and S42 are repeated with respect to all views (i.e., views corresponding to 360° or views corresponding to "180°+fan angles") necessary for reconstruction of a CT image to generate weighted projection data every view.

Figure 12:
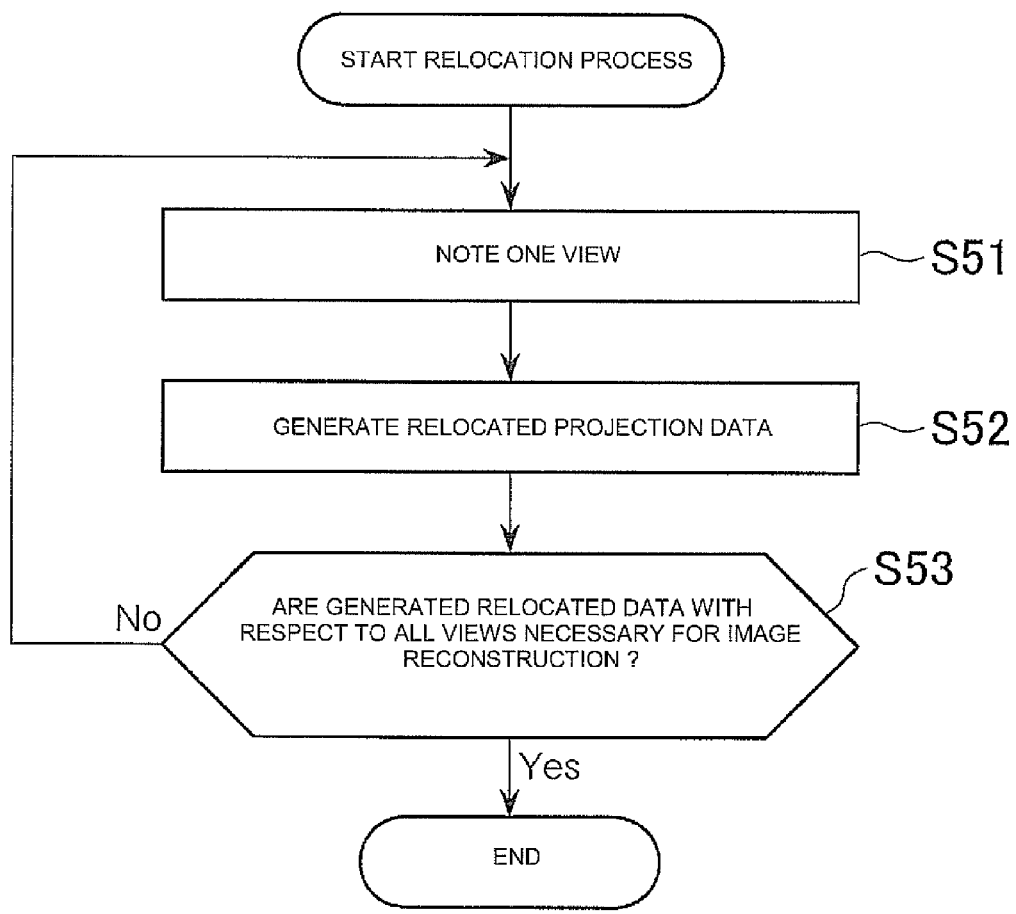
FIG. 12 is a flowchart showing the details of a relocation process.

The relocation process of Step S5 will next be explained in detail with reference to FIG. 12. FIG. 12 is a flowchart showing the details of the relocation process.

At Step S51, attention is given to one of all views (i.e., views corresponding to 360° or views corresponding to "180°+fan angles") necessary for reconstruction of a CT image.

Figure 13:
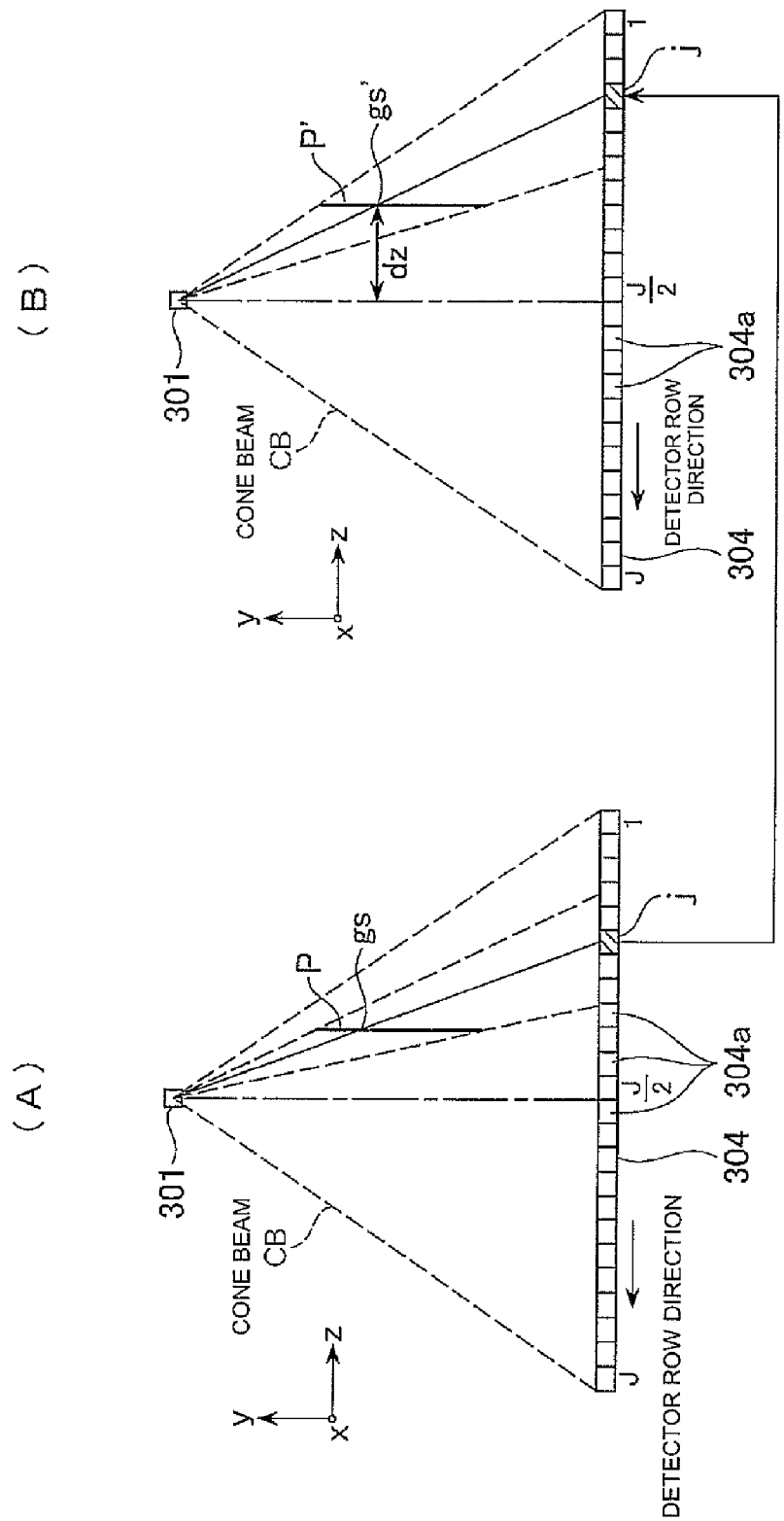
Figure 14:
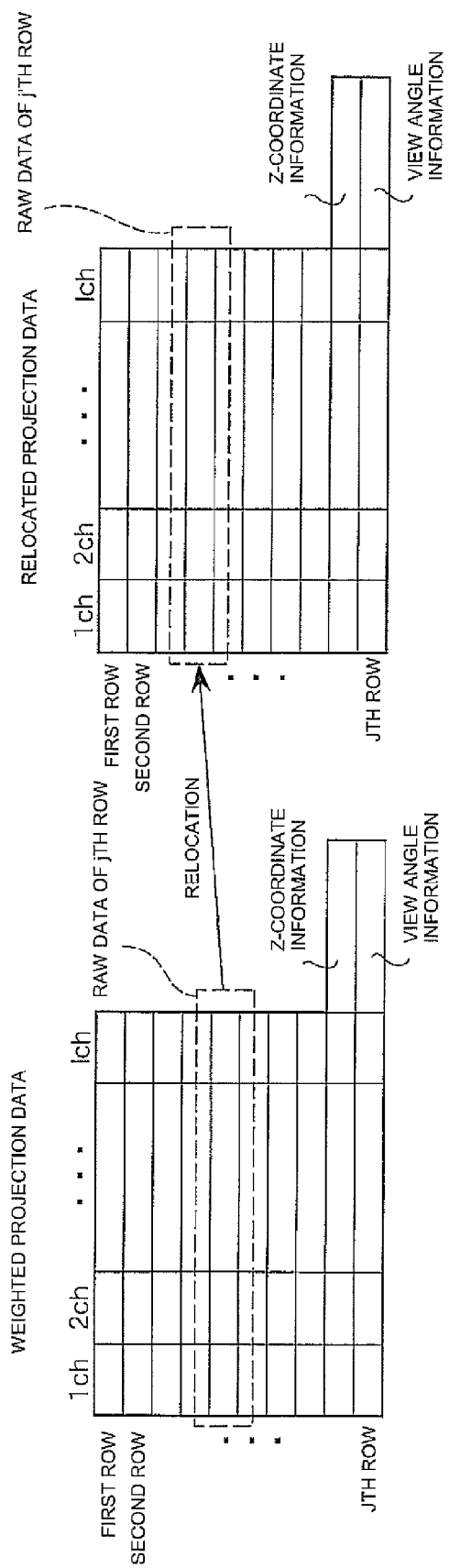
FIG. 14 is a conceptual diagram of the relocation process.

At Step S52, the relocation of each raw data at weighted projection data is performed to generate relocated projection data. This will be explained in more detail using FIGS. 13(A), 13(B), and 14. FIGS. 13(A) and 13(B) are diagrams showing the X-ray tube 301 and the X-ray detector 304 and an image reconstruction plane as viewed from the x-axis direction. A real image reconstruction plane P at the noted view when the cradle 201 is moved under acceleration/deceleration is shown in FIG. 13(A). On the other hand, a virtual image reconstruction plane P' equivalent to the image reconstruction plane P at the noted view where the cradle 201 is assumed to be moved at a constant velocity, is shown in FIG. 13(B). FIG. 14 is a conceptual diagram of a relocation process.

Figure 15:
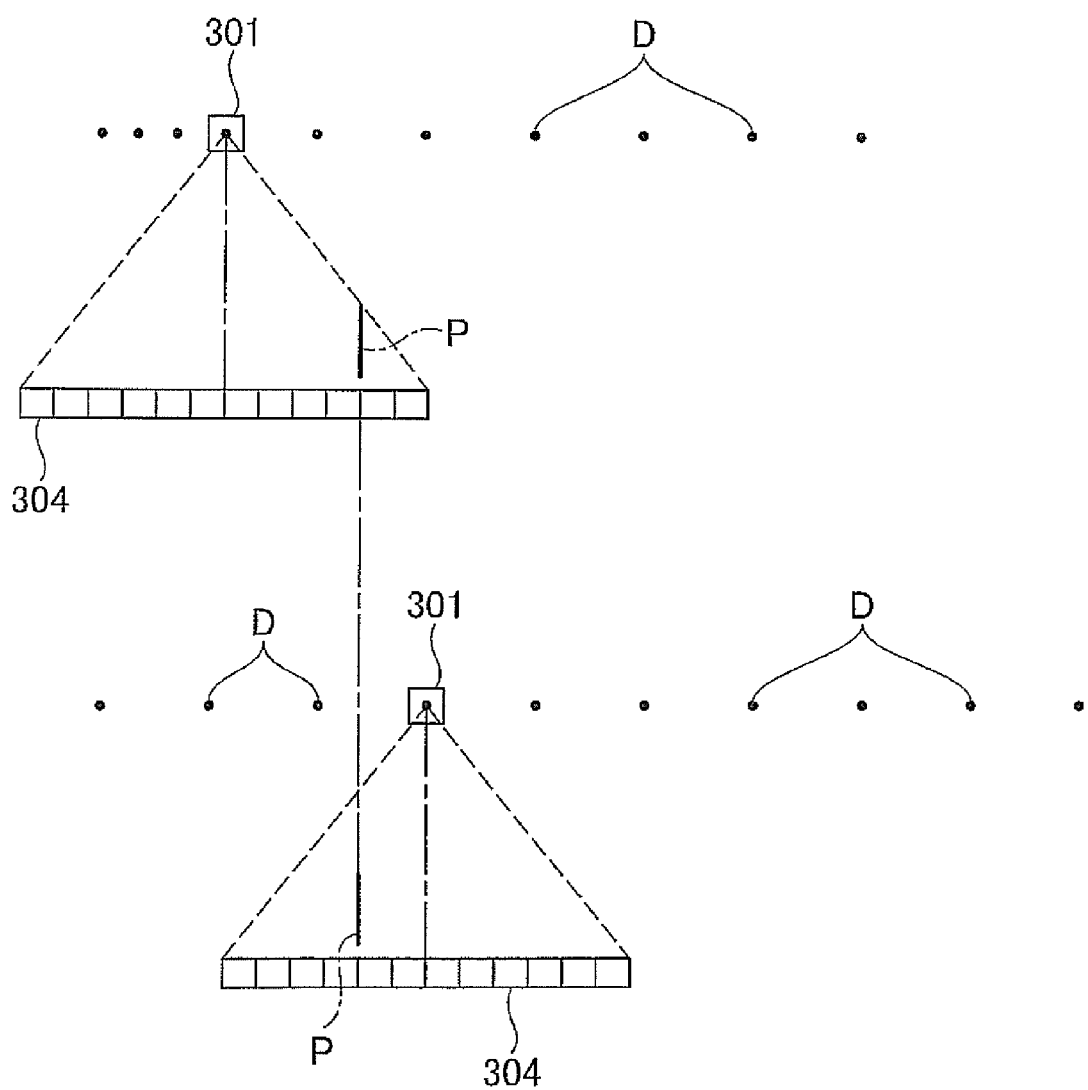
FIG. 15 is a diagram for describing the virtual image reconstruction plane.

The virtual image reconstruction plane P' will now be explained based on FIG. 15. FIG. 15 is a diagram for describing the virtual image reconstruction plane P'. A geometry (above as viewed in the figure) of the X-ray tube 301, the X-ray detector 304 and an image reconstruction plane P at the time that the cradle 201 is moved under acceleration/deceleration, and a geometry (below as viewed in the figure) of the X-ray tube 301, the X-ray detector 304 and the virtual image reconstruction plane P' at the time that the cradle 201 is moved at the constant velocity, are shown in FIG. 15. Dots D shown in the figure indicate trajectories of the X-ray detector 304, and the respective geometries illustrated in the figure are identical to each other in view. The virtual image reconstruction plane P' corresponds to an image reconstruction plane where the cradle 201 is moved at the constant velocity.

Returning back to the description of Step S52 referred to above, raw data corresponding to a pixel group gs on the image reconstruction plane P is relocated as raw data about a pixel group gs' on the virtual image reconstruction plane P', corresponding to the pixel group gs. In other words, raw data of a jth row corresponding to the pixel group gs is relocated as raw data of a j'th row corresponding to the pixel group gs'. At this time, whether the raw data should be relocated as raw data of a detecting element row at any position (i.e., the identification or determination of a detecting element row (j'th row) corresponding to gs') is computed based on a distance dz between the virtual image reconstruction plane P' and the center in the z-axis direction, of the X-ray detector 304, thereby specifying the corresponding detecting element row. This relocation is performed on each raw data at the weighted projection data to generate the relocated projection data.

At Step S53, Steps S51 and S52 are repeated with respect to all views (i.e., views corresponding to 360° or views corresponding to "180°+fan angles") necessary for reconstruction of a CT image to generate relocated projection data every view.

Figure 16:
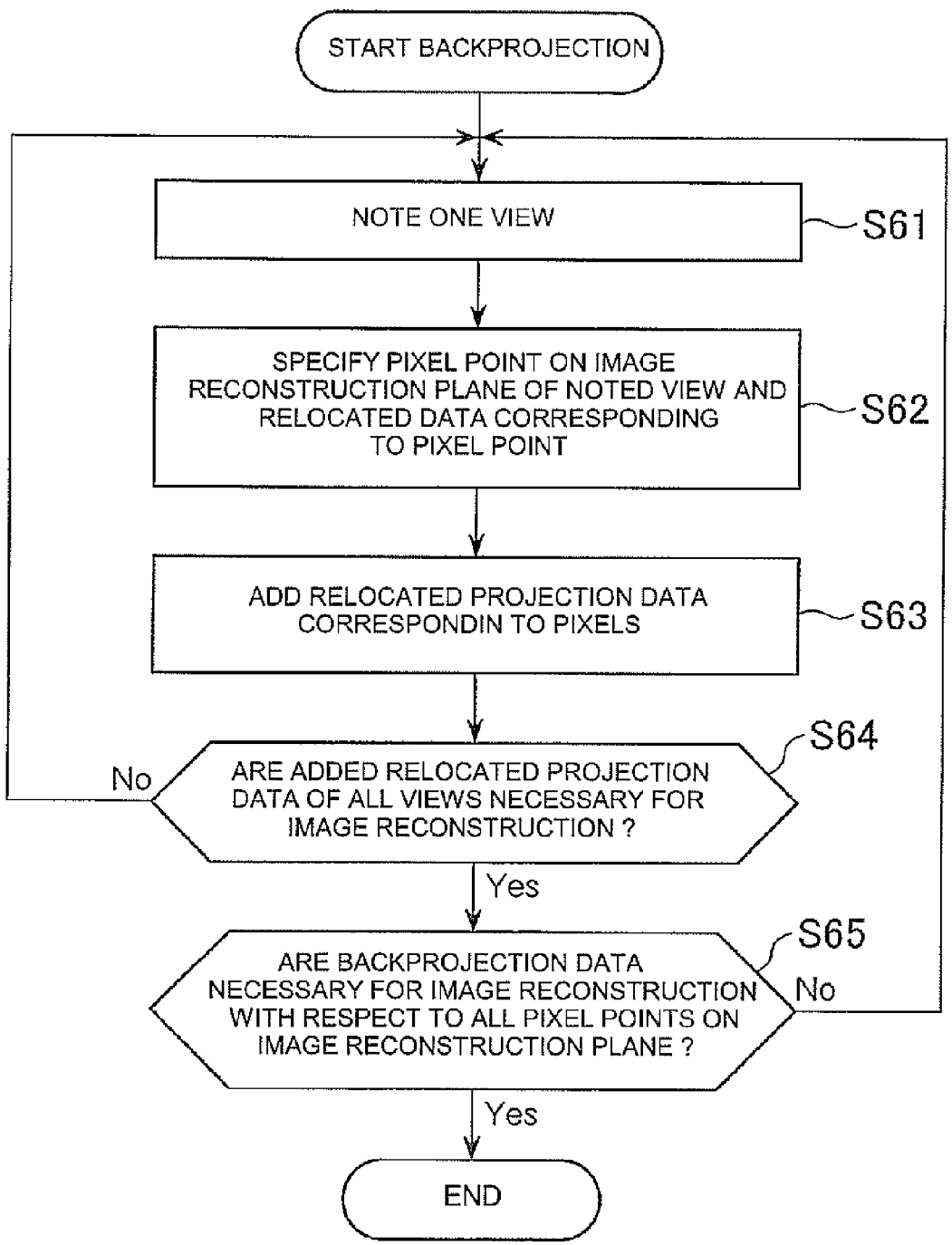
FIG. 16 is a flowchart showing the details of a three-dimensional backprojection process.

A three-dimensional backprojection process of Step S6 will be explained in detail. FIG. 16 is a flowchart showing the details of the three-dimensional backprojection process.

At Step S61, focus on one of all views necessary for reconstruction of a CT image on an image reconstruction plane at a desired image position.

At Step S62, the virtual image reconstruction plane P' at the noted view is assumed. Thereafter, pixel points lying on the virtual image reconstruction plane P' (refer to FIG. 12(B)) and relocated projection data corresponding to the pixel points are identified or specified with reference to the tables shown in FIG. 2.

Figure 17:
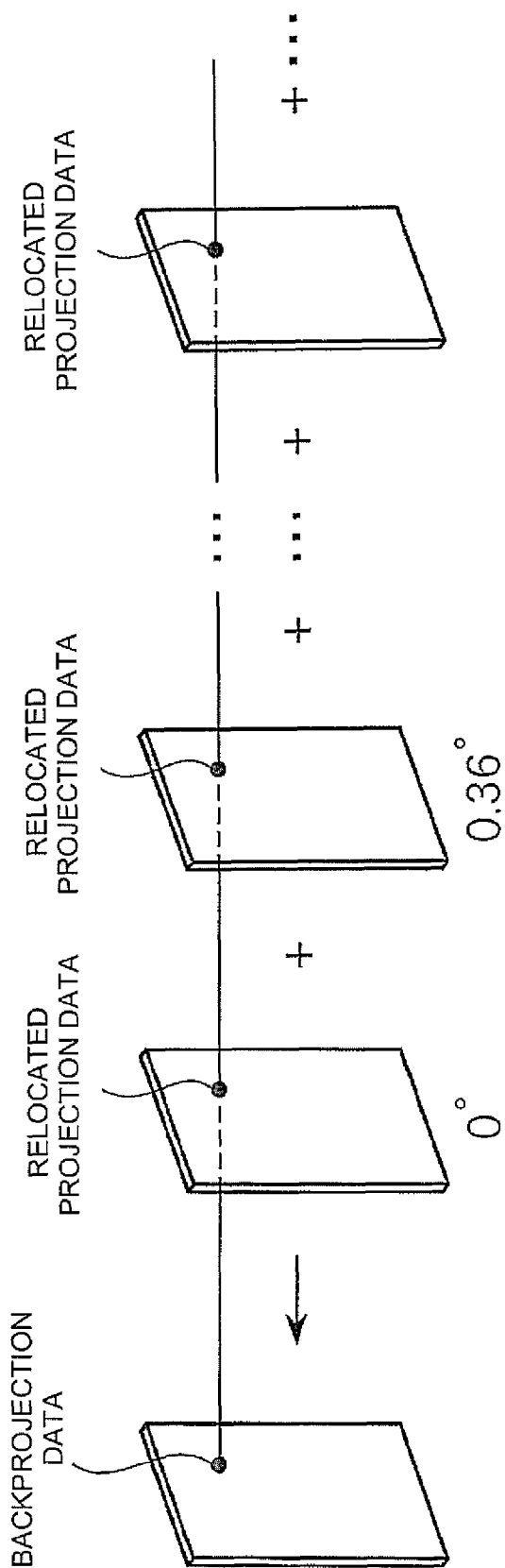
FIG. 17 is an explanatory diagram for indicating that specified relocated projection data are added corresponding to pixels.

At Step S63, the specified relocated projection data are added corresponding to pixels as shown in FIG. 17.

At Step S64, Steps S61 through S63 are repeated with respect to all views (i.e., views corresponding to 360° or views corresponding to "180°+fan angles") necessary for reconstruction of a CT image to generate backprojection data.

At Step S65, Steps S61 through S64 are repeated with respect to all pixel points on the virtual image reconstruction plane P' to obtain backprojection data about all the pixel points on the virtual image reconstruction plane P'.

Although the CT image obtained through Steps S1 through S7 in the above-described manner is one related to the virtual image reconstruction plane P', the virtual image reconstruction plane P' is equivalent to the image reconstruction plane P where the cradle 201 is moved at the constant velocity as described above. Accordingly, the so-obtained CT image results in one lying on a real image reconstruction plane.

According to the first embodiment described above, when image reconstruction is done using projection data acquired upon the movement of the cradle 201 under acceleration/deceleration, a backprojection process is performed on an image reconstruction plane P of each view in assumption of a virtual image reconstruction plane P' where the cradle 201 is assumed to be moved at a constant velocity. Therefore, the amount of computation at the image reconstruction using the projection data acquired when the cradle 201 is moved under acceleration/deceleration can be reduced than conventional. The reduction in the amount of computation in the present embodiment will be described specifically. At Step S5, the relocation process is performed on the raw data at the projection data acquired when the cradle 201 is moved under acceleration/deceleration thereby to specify a pixel point g' lying on a virtual image reconstruction plane P' and projection data corresponding to the pixel point g' by referring to the tables at the backprojection process step of Step S6, whereby a backprojection process can be done. Consequently, the computation for identifying or specifying a pixel point g lying on an image reconstruction plane P and projection data corresponding to the pixel point g becomes unnecessary at the backprojection process step. On the other hand, when raw data corresponding to a pixel group gs on the image reconstruction plane P is relocated as raw data about a pixel group gs' on the virtual image reconstruction plane P', corresponding to the pixel group gs at the relocation process step, the computation of position determination or identification about whether the raw data should be relocated as raw data of a detecting element row at any position, that is, the computation of position identification of the detecting element row (j'th row) corresponding to the pixel group gs' on the virtual image reconstruction plane P' is carried out. However, this computation is done in units of raw data, i.e., units of pixel rows, and the amount of computation is low as compared with the case where computation is done every pixel point at the backprojection process as in the conventional case. Thus, the amount of computation over the entire image reconstructing process can be reduced than conventional, whereby the time taken for image reconstruction can be shortened.

Figure 18:
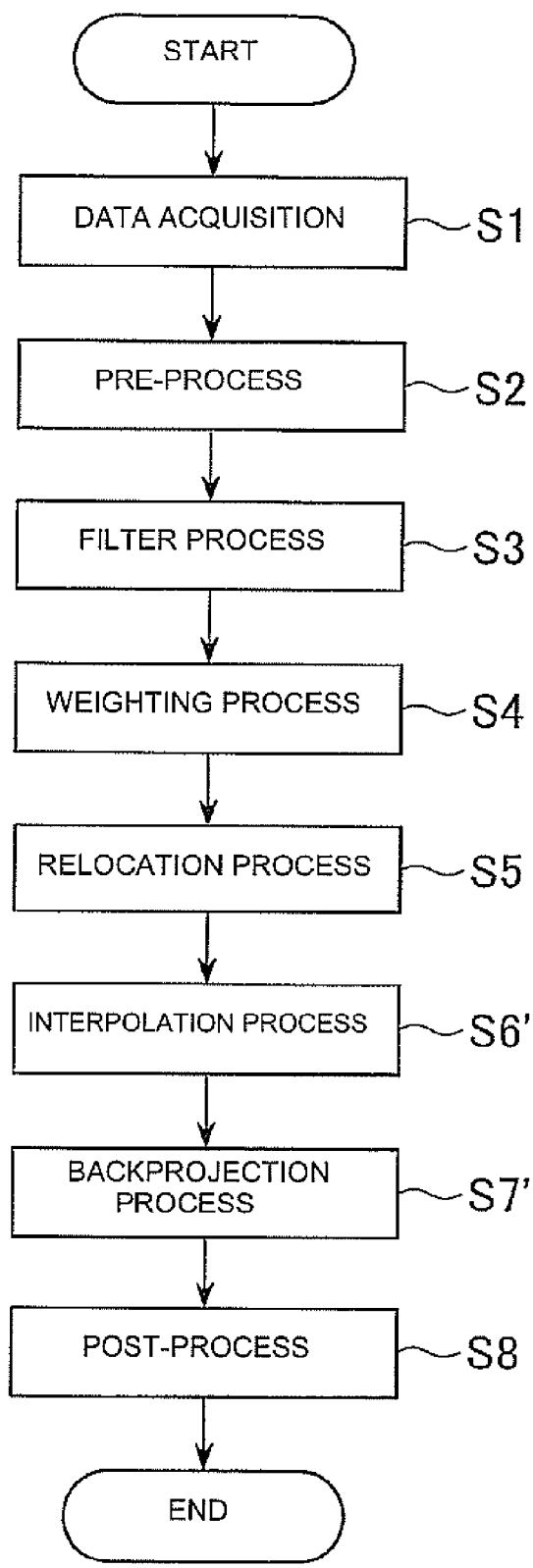
FIG. 18 is a flowchart showing a method of imaging an X-ray CT apparatus according to a second embodiment.

A second embodiment will next be explained. FIG. 18 is a flowchart showing the outline of an imaging method of the X-ray CT apparatus 1 according to the second embodiment. The second embodiment is similar to the first embodiment except that an interpolation process (Step S6') of the relocated projection data is done. In the following description, items similar to those of the first embodiment will not be explained.

The X-ray CT apparatus 1 according to the second embodiment is similar to the first embodiment in construction except that the central processing unit 102 is equipped with unillustrated interpolation processing device in addition to the weighting processing device 1021, the relocation processing device 1022 and the backprojection processing device 1023.

Figure 19:
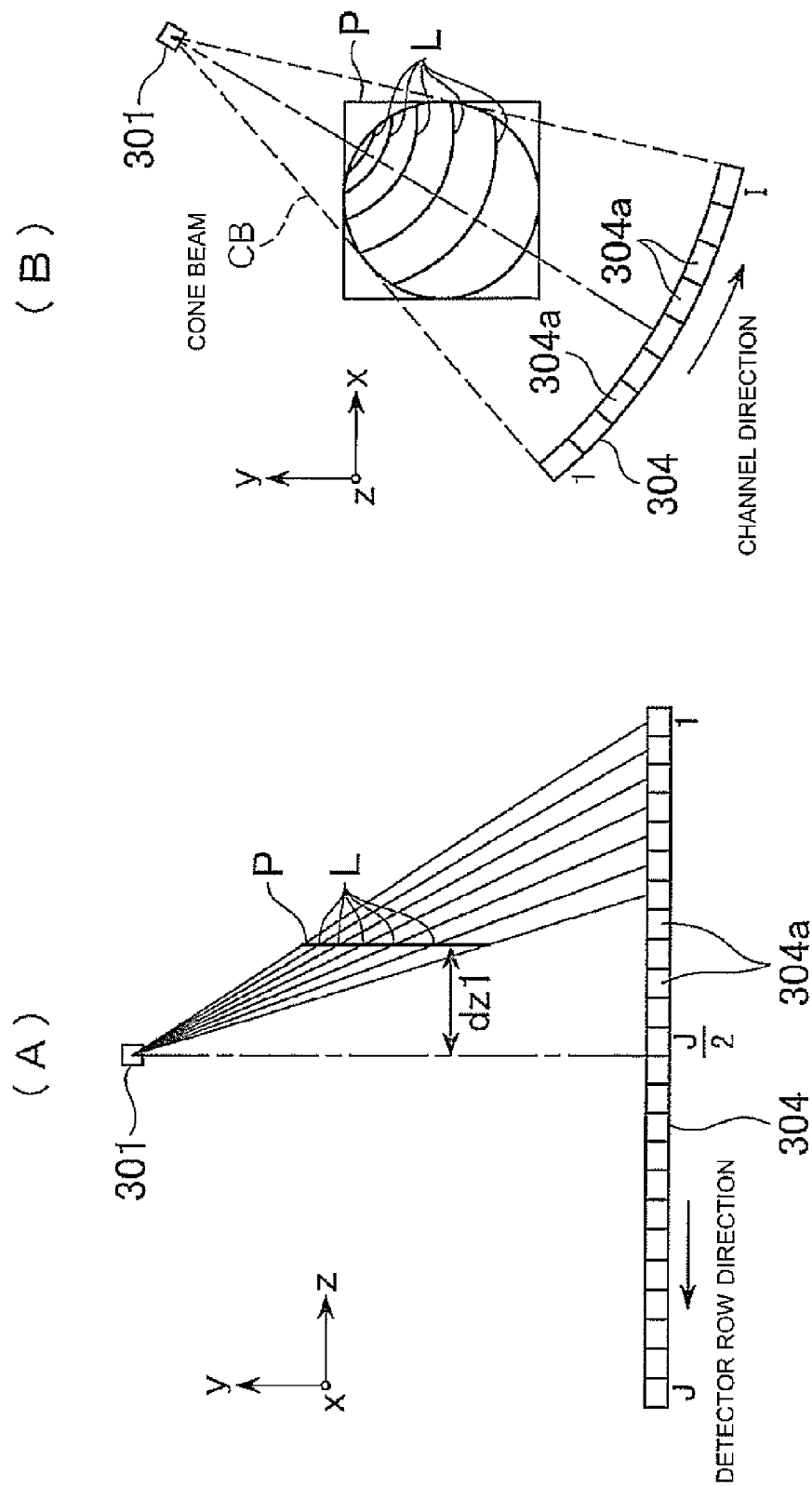
Figure 20:
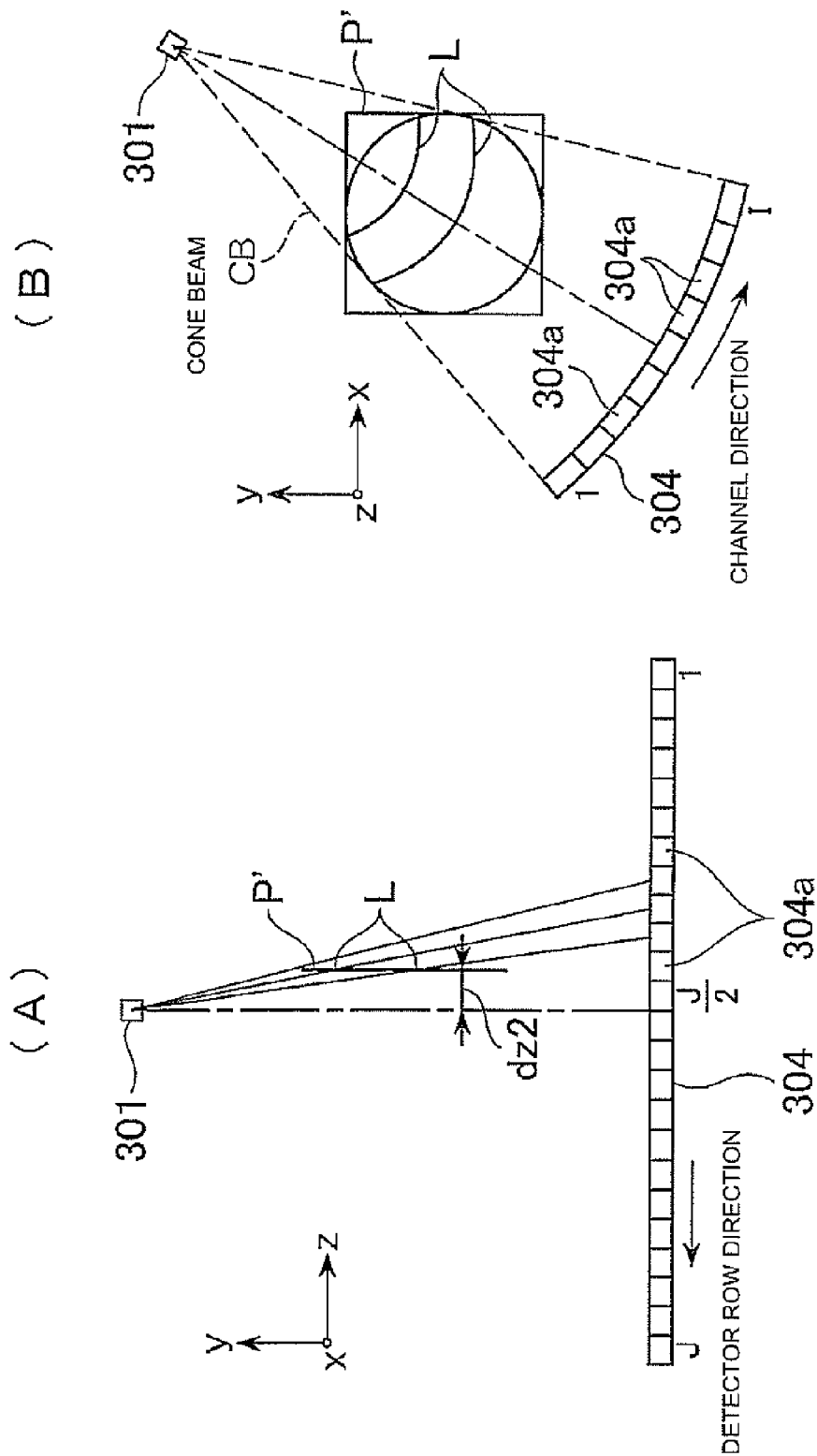

The interpolation process will be explained in detail. FIGS. 19(A), 19(B), 20(A), and 20(B) are diagrams showing the X-ray tube 301 and the X-ray detector 304 and an image reconstruction plane. A real image reconstruction plane P at the noted view when the cradle 201 is moved under acceleration/deceleration is shown in FIGS. 19(A) and 19(B). On the other hand, a virtual image reconstruction plane P' at the noted view where the cradle 201 is assumed to be moved at the constant velocity, is shown in FIGS. 20(A) and 20(B). When a distance dz2 between the center in the z-axis direction, of the X-ray detector 304 and the virtual image reconstruction plane P' is smaller than a distance dz1 between the center in the z-axis direction, of the X-ray detector 304 and the real image reconstruction plane P as shown in FIGS. 19(A), 19(B), 20(A), and 20(B), the density of a distribution L of raw data at relocated projection data generated at the relocation process step of Step S5 becomes small. Thus, in such a case, the relocated projection data is subjected to the interpolation process at Step S6' after the relocation process of Step S5 thereby to enlarge the density of the raw data.

When the interpolation process is performed at Step S6', a backprojection process is performed at Step S7'. While the backprojection process is basically similar to Step S6 in the first embodiment, the backprojection process is performed on the relocated projection data subjected to the interpolation process.

Next, a post-process is performed in a manner similar to Step S7 of the first embodiment at Step S8. That is, the post-process is performed on the backprojection data obtained at Step 7' to obtain a CT image.

According to the second embodiment described above, degradation in image quality can be suppressed by performing the relocated projection data to the interpolation process.

Figure 21:
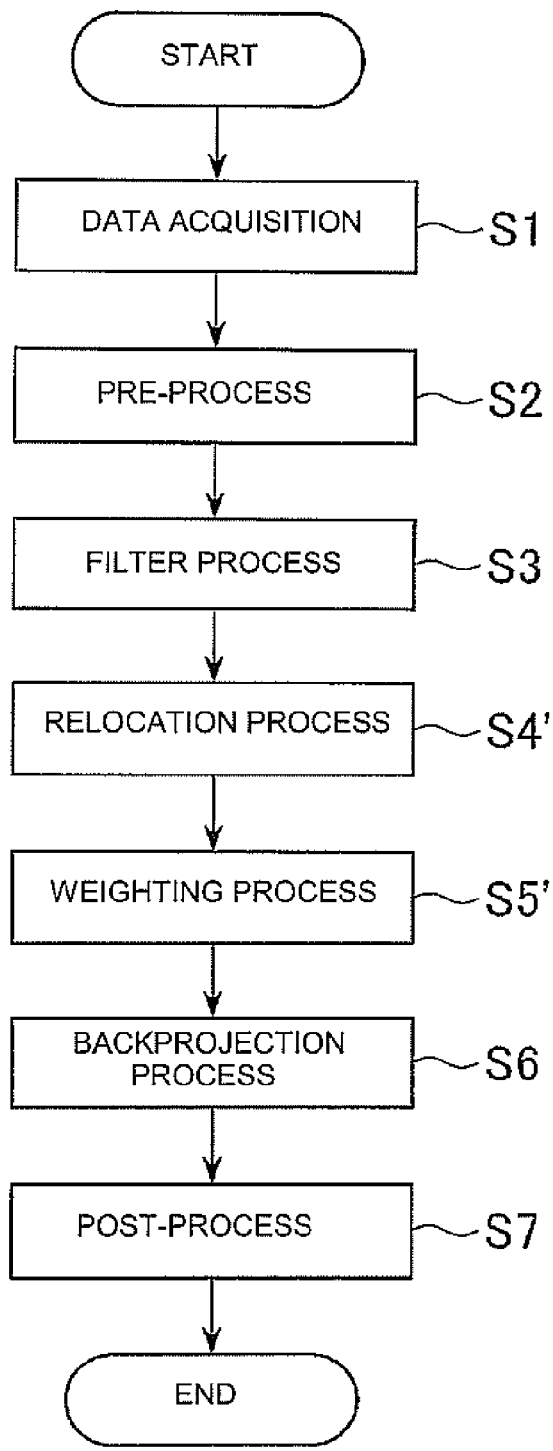
FIG. 21 is a flowchart showing an imaging method of an X-ray CT apparatus according to a third embodiment.

A third embodiment of the present invention will next be explained. FIG. 21 is a flowchart showing an imaging method of the X-ray CT apparatus 1 according to the third embodiment. This flowchart is identical to FIG. 5 except that the flowchart of FIG. 5 and Steps S4 and S5 are changed. Only the changed portions will be explained.

In the third embodiment, the relocation process of projection data is performed at Step S4' subsequent to Step S3 to obtain relocated projection data. The specific contents of the relocation process is similar to the contents of Step S5 described in the first embodiment, and the description thereof will therefore be omitted.

Next, a weighting process is performed on the relocated projection data at Step S5'. While the contents of the weighting process is also basically identical to the contents of Step S4 described in the first embodiment, to which pixel on the image reconstruction plane (i.e., the real image reconstruction plane P in FIG. 13(A)) prior to the relocation process each raw data at the relocated projection data corresponds is computed and thereafter each of the raw data is multiplied by a cone beam reconstruction weight to generate weighted raw data with respect to each raw data, thereby generating relocated projection data subjected to weighting (multiplication process of cone beam reconstruction weight).

At Step S6, a backprojection process is performed on the weighted relocated projection data in a manner similar to each of the embodiments.

Effects similar to the first embodiment can be obtained even by the third embodiment described above.

Figure 22:
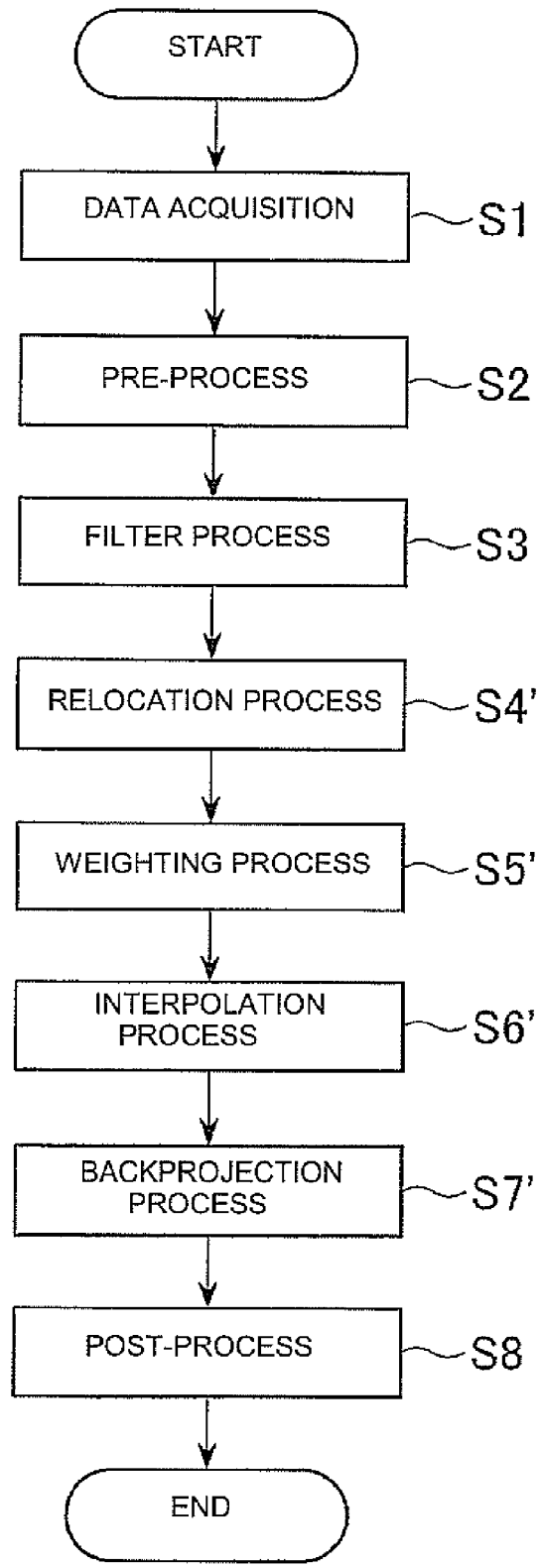
FIG. 22 is a flowchart illustrating an imaging method of an X-ray CT apparatus according to a first modification of the third embodiment.

A modification of the third embodiment will next be explained. A first modification will first be described based on FIG. 22. FIG. 22 is a flowchart showing an imaging method of the X-ray CT apparatus 1 according to the first modification of the third embodiment.

In the first modification, the central processing unit 102 includes interpolation processing device in a manner similar to the second embodiment. The same process as the flowchart shown in FIG. 21 is performed except that an interpolation process is performed as the process of Step S6' after the weighting process of Step S5'. That is, after the weighting process of Step S5', the interpolation process of Step S6' is performed on the weighted relocated projection data. Next, the backprojection process of Step S7' and the post-process of Step S8 are performed after Step S6'.

According to such a first modification of the third embodiment, degradation in image quality can be suppressed by performing the interpolation process in a manner similar to the second embodiment.

Figure 23:
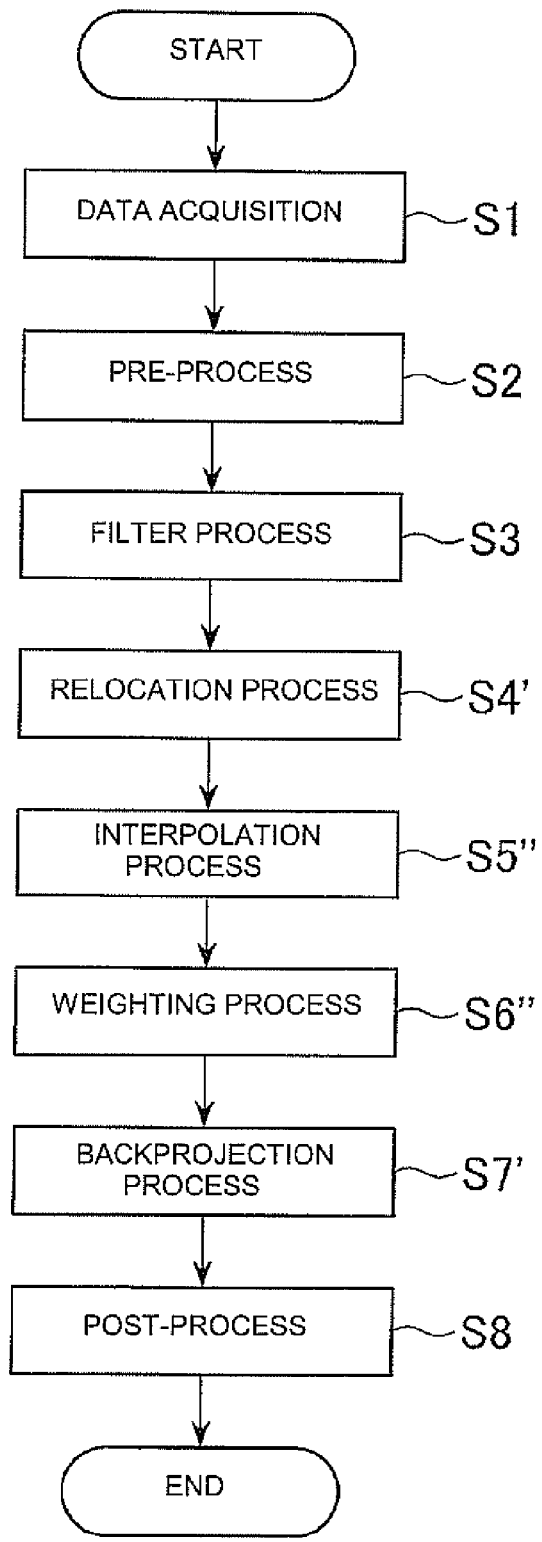
FIG. 23 is a flowchart showing an imaging method of an X-ray CT apparatus according to a second modification of the third embodiment.

A second modification of the third embodiment will next be explained. FIG. 23 is a flowchart showing an imaging method of the X-ray CT apparatus 1 according to the second modification of the third embodiment.

While an interpolation process is performed even in the second modification, this interpolation process is carried out as a process of Step 5" after the relocation process of Step S4'. After the interpolation process is performed on the relocated projection data at Step S5", a weighting process is performed at Step S6". While the contents of the weighting process is also basically similar to the contents of Step S4 described in the first embodiment, to which pixel on an image reconstruction plane prior to the relocation process each raw data at the relocated projection data subsequent to the interpolation process corresponds is computed. Thereafter, each of the raw data is multiplied by a cone beam reconstruction weight to generate weighted raw data with respect to each raw data, thereby generating weighted relocated projection data (multiplication process of cone beam reconstruction weight). After this Step S6", the backprojection process of Step S7' and the post-process of Step S8 are carried out.

Degradation in picture quality can be suppressed by the interpolation process in a manner similar to the second embodiment even by the second modification of the third embodiment.

While the present invention has been described above by the respective embodiments, the present invention is not limited to these. Although each of the embodiments has explained the example of the three-dimensional image reconstructing method, a two-dimensional image reconstructing method which specifies each pixel point on an image reconstruction plane and projection data corresponding to the pixel point and performs a backprojection process thereon, is also applicable in like manner. When a weighting process is performed prior to a relocation process in this case, respective projection data about opposite views with an image reconstruction plane P interposed therebetween or two views different at 360° from each other are respectively multiplied by weight coefficients each based on the distance between the X-ray detector 304 having detected each of the projection data and the image reconstruction plane P, as reconstruction weights to generate weighted projection data every view, whereby two-dimensional image reconstruction is performed. When the weighting process is performed after the relocation process, respective relocated projection data about views with the virtual image reconstruction plane P' interposed therebetween or two views different at 360° from each other are respectively multiplied by weight coefficients each based on the distance between the X-ray detector 304 having detected projection data prior to the relocation corresponding to the respective relocated projection data and the image reconstruction plane P, as the reconstruction weights to generate weighted relocated projection data, whereby two-dimensional image reconstruction is done.

Although the present embodiment has explained the fan image reconstruction, the present invention is applicable even to parallel beam image reconstruction in like manner.

In other respects, it is needless to say that various changes can be made within the scope that does not change the gist of the present invention.

What is claimed is:

1. An X-ray CT apparatus comprising:
a cradle configured to move in a horizontal direction to convey a subject to a photography space;
an X-ray detector comprising a plurality of detecting element rows, configured to obtain projection data by a helical scan when said cradle is moved under one of an acceleration and a deceleration and at a constant velocity; and
a backprojection processing device configured to perform a backprojection process on the projection data, wherein when image reconstruction is carried out using the projection data, said backprojection processing device is further configured to assume a virtual image reconstruction plane where said cradle is assumed to be moved at the constant velocity, with respect to an image reconstruction plane of each view and to backproject projection data onto the virtual image reconstruction plane.

2. The X-ray CT apparatus according to claim 1, further comprising:
a relocation processing device configured to perform a relocation with raw data corresponding to a specific pixel on the image reconstruction plane as raw data about each pixel on the virtual image reconstruction plane, corresponding to the specific pixel, said relocation processing device further configured to perform the relocation process on each raw data at projection data of the specific view to generate relocated projection data and to generate the relocated projection data with respect to all views; and
a storage unit configured to store tables that include pixel points on the virtual image reconstruction plane and X-ray detecting elements corresponding to the pixel points, wherein said backprojection processing device is configured to specify pixel points on the virtual image reconstruction plane and projection data corresponding to the pixel points with respect to the relocated projection data by referring to the tables thereby to perform a backprojection process.

3. The X-ray CT apparatus according to claim 2, further comprising an interpolation processing device configured to perform an interpolation process on the relocated projection data, wherein said backprojection processing device is configured to specify pixel points on the virtual image reconstruction plane and projection data corresponding to the pixel points with respect to the relocated projection data subsequent to the interpolation process by referring to the tables thereby to perform a backprojection process.

4. The X-ray CT apparatus according to claim 2, further comprising a weighting processing device configured to multiply the projection data by reconstruction weights in order to generate weighted projection data every view, wherein said relocation processing device is configured to perform a relocation process on each raw data at the weighted projection data.

5. The X-ray CT apparatus according to claim 4, wherein said weighting processing device is configured to specify to which pixel on the image reconstruction plane each raw data at the projection data corresponds and thereafter to perform a multiplication process of a cone beam reconstruction weight to generate weighted projection data.

6. The X-ray CT apparatus according to claim 4, wherein said weighting processing device is configured to multiply respective projection data about opposite views with an image reconstruction plane interposed therebetween or two views different at 360° from each other by weight coefficients each based on a distance between said X-ray detector having detected the projection data and the image reconstruction plane as the reconstruction weights to generate weighted projection data every view.

7. The X-ray CT apparatus according to claim 2, further comprising a weighting processing device configured to multiply the relocated projection data by reconstruction weights after the relocation process in order to generate weighted relocated projection data, wherein said backprojection processing device is configured to perform a backprojection process on the weighted relocated projection data.

8. The X-ray CT apparatus according to claim 7, wherein said weighting processing device is configured to specify to which pixel on the image reconstruction plane prior to the relocation process each raw data at the relocated projection data corresponds and thereafter to perform a multiplication process of a cone beam reconstruction weight in order to generate weighted relocated projection data.

9. The X-ray CT apparatus according to claim 7, wherein said weighting processing device is configured to multiply respective relocated projection data about one of opposite views with the virtual image reconstruction plane interposed therebetween and two views different at 360° from each other by weight coefficients each based on a distance between said X-ray detector having detected the projection data prior to the relocation, corresponding to the relocated projection data and the image reconstruction plane as the reconstruction weights in order to generate weighted relocated projection data.

10. The X-ray CT apparatus according to claim 2, further comprising a weighting processing device configured to multiply the relocated projection data by reconstruction weights after the relocation process in order to generate weighted relocated projection data, and an interpolation processing device configured to perform an interpolation process on the weighted relocated projection data, wherein said backprojection processing device is configured to perform a backprojection process on the relocated projection data subjected to the weighting process and the interpolation process.

11. The X-ray CT apparatus according to claim 10, wherein said weighting processing device is configured to specify to which pixel on the image reconstruction plane prior to the relocation process each raw data at the relocated projection data corresponds and thereafter to perform a multiplication process of a cone beam reconstruction weight in order to generate weighted relocated projection data.

12. The X-ray CT apparatus according to claim 10, wherein said weighting processing device is configured to multiply respective relocated projection data about one of opposite views with the virtual image reconstruction plane interposed therebetween and two views different at 360° from each other by weight coefficients each based on a distance between said X-ray detector having detected the projection data prior to the relocation, corresponding to the relocated projection data and the image reconstruction plane as the reconstruction weights in order to generate weighted relocated projection data.

13. The X-ray CT apparatus according to claim 2, further comprising an interpolation processing device configured to perform an interpolation process on the relocated projection data after the relocation process, and a weighting processing device configured to multiply the relocated projection data subjected to the interpolation process by reconstruction weights to perform a weighting process, wherein said backprojection processing device is configured to perform a backprojection process on the relocated projection data subjected to the interpolation process and the weighting process.

14. The X-ray CT apparatus according to claim 13, wherein said weighting processing device is configured to specify to which pixel on the image reconstruction plane prior to the relocation process each raw data at the relocated projection data corresponds and thereafter to perform a multiplication process of a cone beam reconstruction weight in order to generate weighted relocated projection data.

15. The X-ray CT apparatus according to claim 13, wherein said weighting processing device is configured to multiply respective relocated projection data about one of opposite views with the virtual image reconstruction plane interposed therebetween and two views different at 360° from each other by weight coefficients each based on a distance between said X-ray detector having detected the projection data prior to the relocation, corresponding to the relocated projection data and the image reconstruction plane as the reconstruction weights in order to generate weighted relocated projection data.

16. An image reconstruction method for reconstructing an image using an X-ray CT apparatus that includes a cradle and an X-ray detector having a plurality of detecting element rows, said method comprising:
   moving the cradle in a horizontal direction to convey a subject to a photography space, the cradle moved under one of an acceleration and a deceleration and at a constant velocity;
   obtaining projection data by a helical scan via the plurality of detecting element rows while the cradle is moving;
   performing a backprojection process on the projection data; and
   reconstructing the image using the projection data, wherein the during the back projection process a virtual image reconstruction plane is assumed where the cradle is assumed to be moved at the constant velocity with respect to an image reconstruction plane of each view and backprojecting projection data onto the virtual image reconstruction plane.

17. The image reconstruction method according to claim 16, further comprising performing a relocation with raw data corresponding to a specific pixel on the image reconstruction plane as raw data about each pixel on the virtual image reconstruction plane, corresponding to the specific pixel and which performs the relocation process on each raw data at projection data of the specific view to generate relocated projection data and generates the relocated projection data with respect to all views, wherein performing a backprojection process comprises specifying pixel points on the virtual image reconstruction plane and projection data corresponding to the pixel points with respect to the relocated projection data by referring to the tables in which pixel points on the virtual image reconstruction plane and X-ray detecting elements corresponding to the pixel points being stored thereby to perform a backprojection process.

18. The image reconstruction method according to claim 17, further comprising performing an interpolation process on the relocated projection data, wherein performing a backprojection process comprises specifying pixel points on the virtual image reconstruction plane and projection data corresponding to the pixel points with respect to the relocated projection data subsequent to the interpolation process by referring to the tables thereby to perform a backprojection process.

19. The image reconstruction method according to claim 17, further comprising multiplying the projection data by reconstruction weights to generate weighted projection data every view, wherein performing a relocation comprises performing a relocation process on each raw data at the weighted projection data.

20. The image reconstruction method according to claim 19, wherein multiplying the projection data comprises specifying to which pixel on the image reconstruction plane each raw data at the projection data corresponds and thereafter performs a multiplication process of a cone beam reconstruction weight to generate weighted projection data.

* * * * *